United States Patent [19]

Hamanaka

[11] Patent Number: 4,619,783
[45] Date of Patent: Oct. 28, 1986

[54] PROCESS AND INTERMEDIATES FOR THE PREPARATION OF PENEM DERIVATIVES

[75] Inventor: Ernest S. Hamanaka, Gales Ferry, Conn.

[73] Assignee: Pfizer Inc., New York, N.Y.

[21] Appl. No.: 502,895

[22] Filed: Jun. 10, 1983

[51] Int. Cl.$^4$ .................. C07D 205/08; C07D 403/12; C07D 498/04; C07D 401/12
[52] U.S. Cl. .................................... 540/361; 540/310; 540/357; 540/359; 540/360
[58] Field of Search .......... 260/239 AL, 245.4, 330.3, 260/330.9; 544/3, 54, 58.2, 58.4, 58.5, 63, 69, 96, 98, 111, 179, 180, 182, 212, 215, 219, 220, 229, 238, 301, 311, 312, 316, 317, 319–323, 325, 326, 327, 332, 335, 336, 354, 406–408; 546/208, 275

[56] References Cited

FOREIGN PATENT DOCUMENTS

| | | |
|---|---|---|
| 881012 | 1/1979 | Belgium . |
| 887886 | 3/1980 | Belgium . |
| 58317 | 2/1981 | European Pat. Off. . |
| 70204 | 7/1981 | European Pat. Off. . |
| 51813 | 5/1982 | European Pat. Off. . |
| 69377 | 1/1983 | European Pat. Off. . |
| 91576 | 10/1983 | European Pat. Off. . |
| 7176988 | 4/1981 | Japan . |
| 7197280 | 5/1981 | Japan . |
| 7200392 | 6/1981 | Japan . |
| 7200394 | 6/1981 | Japan . |
| 2013674 | 2/1978 | United Kingdom . |

OTHER PUBLICATIONS

Kametani, Chem Abs 91, 39213u (1979).
Reese et al, "Protective Groups in Organic Chemistry" (pp. 95–142), 1973.
Haines, Adv. Carbohydrate Chem 33, 11–109 (1976).
Hayashi et al., 2-(Alkylthio)penem-3-carboxylic Acids. V., *Chem. Pharm. Bull.,* 29(11), 3158–3172 (1981).
Yoshida et al., 2-(Alkylthio)penem-3-carboxylic Acids. IV., *Chem. Pharm. Bull.,* 29(10, 2899–2909 (1981).
Volante, A, New Highly Efficient Method for the Conversion of Alcohols to Thioesters and Thiols, *Tetrahedron Letters,* 22(33), 3119–3122 (1981).
Oida et al., 2-(Alkylthio)penem-3-carboxylic Acids. II., *Chem. Pharm. Bull.,* 28(11), 3258–3264 (1980).
DeNinno, et al., A Convenient Synthesis of Racemic 6-Hydroxyethyl-2-Alkylthio-Substituted Penems, *Tetrahedron Letters,* 28(35), 3535–3538 (1982).
Tanaka et al., 2-Thioxopenams, Useful Intermediate for Penem Synthesis,*Chem. Comm.,* 1982(13), 713–714 (1982).
J. L. .Wardell, Preparation of Thiols, in the Chemistry of the Thiol Group, S. Patai, Ed., John Wiley & Sons, London, 1974, Chapt. 4.
A. Afonso, et al., New Synthesis of Penems, the Oxalimide Cyclization Reaction, *J. Amer. Chem. Soc.,* 104, 6138–6139(1982).

Primary Examiner—Mark L. Berch
Attorney, Agent, or Firm—Charles J. Knuth; Albert E. Frost; Peter C. Richardson

[57] ABSTRACT

Certain substituted-2-penem-3-carboxylic acid compounds, and pharmaceutically-acceptable salts thereof, can be prepared from the appropriate xanthate or trithiocarbonate by desulfurization, followed by halogenation and ring closure. The corresponding desulfurized and halogenated intermediates are disclosed.

8 Claims, No Drawings

PROCESS AND INTERMEDIATES FOR THE PREPARATION OF PENEM DERIVATIVES

BACKGROUND OF THE INVENTION

This invention is directed to the preparation of derivatives of the family of antibacterial agents incorporating a 2-azetidinone (beta-lactam) ring. Chemically, the antibacterial agents are identified as 2-substituted-2-penem-3-carboxylic acid compounds.

2-Substituted-2-penem-3-carboxylic acid compounds have been disclosed in U.S. Pat. No. 4,155,912; Belgian Pat. No. 866,845; published European Patent Applications 636 and 2,210; and *Journal of the American Chemical Society*, 101, 2210 (1979). According to the abstract thereof published by Derwent Publications Ltd., published Japanese patent application No. 66694/1979 also discloses 2-substituted-2-penem-3-carboxylic acid compounds.

SUMMARY OF THE INVENTION

This invention is directed to a method for preparing compounds of the formula

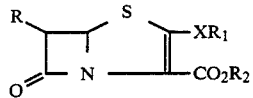

or a pharmaceutically acceptable salt thereof, wherein:

R is hydrogen, 1-hydroxyalkyl having 1 or 2 carbon atoms or wherein the 1-hydroxyalkyl is substituted with a hydroxyl-protecting group;

$R_1$ is (alk)-G, (alk)-$G_1$, $G_1$ or CH($G_2$)$_2$ wherein (alk) is an alkyl group having one to four carbon atoms;

G is hydrogen, alkoxy having one to five carbon atoms, 2-(alkoxy)ethoxy having three to seven carbon atoms, alkylthio having one to five carbon atoms, phenoxy, thiophenoxy, azido, amino, amino substituted with an amine-protecting group, N-phenyl-N-alkylamino wherein the alkyl has one to four carbon atoms, N-alkanoylamino having two to six carbon atoms, N-alkoxyalkanoylamino having three to ten carbon atoms, 2-(N-alkanoylamino)ethoxy having four to eight carbon atoms, aminocarbonyl, aminocarbonyloxy, N-alkylaminocarbonylamino having two to five carbon atoms, alkanoylaminoacetylamino having four to seven carbon atoms, N-alkylaminocarbonyloxy, aminocarbonylalkoxy having two to five carbon atoms, N-alkylaminocarbonyl having two to five carbon atoms, N-(alkoxyalkyl)aminocarbonyl having three to nine carbon atoms;

$G_1$ is azetidinyl or azetidinyl substituted with N-alkanoyl having two to six carbon atoms or an amine-protecting group; a five- or six-membered ring which is carbocyclic or heterocyclic having one or two oxygen atoms, one, two, three or four nitrogen atoms, a sulfur atom, a nitrogen atom and an oxygen atom or a nitrogen atom and a sulfur atom, or said five- or six-membered ring substituted with alkyl having one to four carbon atoms, dialkyl each having one to four carbon atoms, oxo, amino, amino substituted with an amine-protecting group, alkoxycarbonyl having two to five carbon atoms, di(alkoxycarbonyl) each having two to five carbon atoms, aminocarbonyl, alkoxyalkyl having two to seven carbon atoms, phenyl, formyl, N-alkylaminocarbonyl having 2-5 carbon atoms, alkylaminocarbonylamino having two to five carbon atoms, alkanoylamino having two to five carbon atoms, alkoxy having one to four carbon atoms or phenoxyacetyl;

$G_2$ is alkanoylaminomethyl each having three to seven carbon atoms or alkoxy each having one to four carbon atoms.

$R_2$ is hydrogen, and ester group which is hydrolyzed in vivo or a carboxylic acid protecting group; and X is oxygen or sulfur;

wherein the compound is prepared by the steps of:

(a) desulfurizing a first beta lactam of the formula

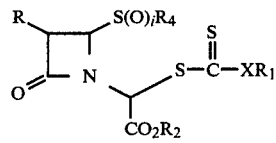

to obtain a second beta lactam of the formula

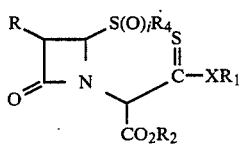

wherein:

$R_4$ is alkyl having 1-7 carbon atoms or alkyl substituted with alkoxy having 1-4 carbon atoms, phenyl, pyridyl or 2-benzothiazolyl; and i is zero or 1;

(b) halogenating the beta lactam of formula VII to obtain a third beta lactam of the formula

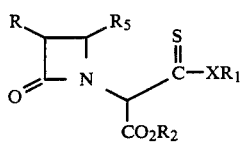

wherein $R_5$ is chloro, bromo or iodo; and (c) cyclizing the beta lactam of formula III to obtain said compound.

Included within the invention is the method wherein the hydroxyl-protecting group is benzyloxycarbonyl, p-nitrobenzyloxy-carbonyl, allyloxycarbonyl, 2,2,2-trichcloroethoxycarbonyl or trialkylsilyl wherein each alkyl has 1-6 carbon atoms. When the hydroxy-protecting group is trialkylsilyl, the method may comprise the additional step of removing the hydroxyl-protecting group with a tetralkylammonium compound wherein each alkyl has 1-7 carbon atoms. Preferably, the tetraalkylammonium compound is a fluoride salt.

The carboxylic acid protecting group may be benzyl, p-nitrobenzyl, allyl or 2,2,2-trichloroethyl.

Within the method, the amine-protecting group may be benzyloxycarbonyl, p-nitrobenzyloxycarbonyl, allyloxycarbonyl, 2,2,2-trichloroethoxycarbonyl or together with the amine nitrogen atom being protected azido.

The method may include the additional step of removing the hydroxyl-protecting group, carboxyl-protecting group or amine-protecting group by hydrogenation treatment with zinc or treatment with tetrakis(triphenylphosphine)palladium.

In step (a) a base or a base and trivalent phosphorus compound may be employed. The preferred base is sodium hydride. The trivalent phosphorus compound is preferably trialkylphosphine, triarylphosphine or trialkylphosphite, more preferably triphenylphosphine.

In step (c) a base may be employed. Preferred bases include a trialkylamine wherein each alkyl has 1–4 carbon atoms or a tetralkylammonium hydroxide wherein each alkyl has 1–7 carbon atoms. More preferably the base is diisopropylethylamine.

The present method includes the preparation of compounds wherein R is hydrogen, X is oxygen and $R_1$ is methyl, ethyl, 2-methoxyethyl, 2-ethoxyethyl, 1-methoxy-2-propyl, bis(methoxymethyl)methyl, 2-(2-methoxyethoxy)ethyl, 2-azidoethyl, aminocarbonylmethyl, 1-(aminocarbonyl)-1-ethyl, 1-(N-methylaminocarbonyl)-1-ethyl, bis(acetyl-aminomethyl)methyl, 2-(aminocarbonylmethoxy)ethyl, 2-(N-methylaminocarbonyloxy)ethyl, 1-(N-(2-methoxyethyl)aminocarbonyl)-1-ethyl, 2-(aminocarbonyloxy)ethyl, 2-(N-methylaminocarbonylamino)ethyl, 2-(methoxymethylcarbonylamino)ethyl, 2-(acetylaminoacetylamino)ethyl, 2-(2-acetylaminoethoxy)ethyl, 1-acetylamino-2-propyl, 2-(acetylamino)ethyl, 2-azidocyclohexyl, 2-methoxycyclohexyl, 2-formylaminocyclohexyl, 2-acetylaminocyclohexyl, 2-(N-methylaminocarbonylamino)-cyclohexyl, 2-methoxycyclopentyl, 1-acetyl-3-azetidinyl, 1-acetyl-3-pyrrolidinyl, 1-ethylcarbonyl-3-pyrrolidinyl, 1-formyl-3-pyrrolidinyl, 2-pyrrolidon-3-yl, 3-tetrahydrofuranyl, 2-tetrahydrofuranylmethyl, 2-(1-imidazolyl)ethyl, 2-(4-methoxycarbonyl-1,2,3-triazolyl)ethyl, 2-(4,5-dimethoxycarbonyl-1,2,3-triazolyl)ethyl, 2-(4-aminocarbonyl-1H-1,2,3-triazolyl)ethyl, 1,3-dioxolan-2-ylmethyl, 1,3-dioxolan-4-ylmethyl, 2,2-dimethyl-1,3-dioxolan-4-ylmethyl, 3-methyl-1,3-oxazolid-2-on-4-ylmethyl, 2-(2H-1,2,3,4-tetrazol-2-yl)ethyl, 2-piperidon-5-yl, 1-methyl-2-piperidon-3-yl, 1-formyl-3-piperidyl, 1-formyl-4-piperidyl, 1-acetyl-3-piperidyl, 1-phenoxymethylcarbonyl-3-piperidyl, 1-ethylcarbonyl-3-piperidyl, 1-aminocarbonyl-3-piperidyl, 1-aminocarbonylmethyl-2-piperidon-3-yl, 2-perhydropyrimidinon-5-yl, 1,3-dioxan-5-yl, 2-phenyl-1,3-dioxan-5-yl, 2-methoxymethyl-1,3-dioxan-5-yl, 2-phenoxyethyl, 2-thiophenoxyethyl, 2-phenethyl, 2-(2-thienyl)ethyl, 2-(2-pyridyl)ethyl, 3-(3-pyridyl)propyl, 2-(pyrazolinyl)ethyl, 2-(4-methylthiazol-5-yl)ethyl, 2-(phthalimido)ethyl, 2-(2-thiazolyl)thioethyl 2-(N-methylanilino)ethyl, 2-(2-tetrahydropyranyloxy)ethyl, 2-tetrahydropyranyl-methyl, 2-(1-morpholino)ethyl, 2-azido-2-phenethyl, 1-acetyl-2-pyrrolidylmethyl, 2-(2-pyrrolidon-1yl)ethyl, 2-(2-pyridinoylamino)ethyl, 2-(2-furanoyl-amino)ethyl, 2-(2-imidazolidinon-1-yl)ethyl 2-piperidon-3-yl or 2-(2-piperidon-1-ylacetylamino)ethyl; preferably $R_2$ is p-nitrobenzyl.

Additional compounds which can be prepared by the present method are those wherein R is 1-hydroxyethyl or 1-hydroxyethyl substituted with a hydroxyl-protecting group, X is oxygen and $R_1$ is 1-formyl-3-piperidinyl, 1,3-dioxan-5-yl 1,3-dioxan-2-yl, 1,3-dioxolan-2-yl, 1,3-dioxolan-4-yl, 1,3-dioxolan-4-ylmethyl, 2-piperidinon-3-yl, 2-piperidinon-5-yl, 2-pyrrolidinon-3-yl, 1-methoxy-2-propyl, 2-methoxyethyl, 3-methyl-1,3-oxazolidin-2-on-4-ylmethyl, 2-tetrahydropyranyl-methyl, 1-methyl-2-piperidinylmethyl or 2-(4-acetyl-1-piperazinyl)ethyl; preferably wherein $R_2$ is p-nitrobenzyl.

Other compounds which can be prepared by the present method are those wherein R is hydrogen, X is oxygen and $R_1$ is 2-azidoethyl, 2-aminoethyl, 1-azido-2-propyl, 1-amino-2-propyl, 1-p-nitrobenzyloxycarbonyl-3-pyrrolidinyl, 3-pyrrolidinyl, 1-p-nitrobenzyloxycarbonyl-3-piperidinyl, 3-piperidinyl, 1-p-nitrobenzyloxycarbonyl-2-pyrrolidinylmethyl, 2-pyrrolidinylmethyl or 2-aminocyclohexyl; preferably wherein $R_2$ is p-nitrobenzyl.

The present invention includes the method wherein $R_2$ is alkanoyloxymethyl having from 3 to 8 carbon atoms, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonly)aminomethyl having from 3 to 9 carbon atoms, 1-(N-[alkoxycarbonyl]amino)ethyl having from 4 to 10 carbon atoms, 3-phthalidyl, 4-crotonolactonyl, gamma-butyrolacton-4-yl or carboxyalkylcarbonyloxymethyl having from 4 to 12 carbon atoms.

The beta lactam of formula VII and the beta lactam of formula III both substituted as previously discussed, are also included with the scope of the present invention.

DETAILED DESCRIPTION OF THE INVENTION

The compounds of formula I are useful as antibacterial agents, or precursors thereof, and are derivatives of the bicyclic nucleus of the formula:

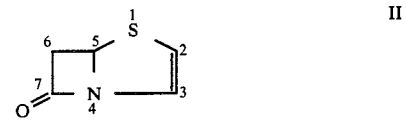

Throughout this specification, the nucleus of formula II is identified by the name "2-penem," and ring atoms are numbered as shown. Also, throughout this specification, the abbreviation "PNB" is used for the p-nitrobenzyl group.

When R is other than hydrogen, the relationship between the hydrogen or bridgehead carbon 5 and the remaining hydrogen on carbon 6 can be cis or trans. The present invention embraces both isomers as well as mixtures thereof. The trans isomer is generally preferred in pharmaceutical applications and the cis isomer can be readily converted to the trans isomer.

As will be appreciated various optically active isomers may exist. The present invention embraces such optically active isomers as well as mixtures thereof.

An ester group which readily hydrolyzes in vivo is intended to refer to non-toxic ester residues which are rapidly cleaved in mammalian blood or tissue to release the corresponding free acid (i.e., the compound of formula I wherein $R_2$ is hydrogen). Typical examples of such readily hydrolyzable ester-forming residues which can be used for $R_2$ are alkanoyloxymethyl having from 3 to 8 carbon atoms, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-[alkoxycarbonyl]amino)ethyl having from 4 to 10 carbon atoms, 3-phthalidyl, 4-crotonolactonyl or gamma-butyrolacton-4-yl. Another class of esters which readily hydrolyze in vivo are the carboxyalkylcarbonyloxymethyl esters having from 4 to 12 carbon atoms; a pharmaceutically acceptable cation may be employed with these esters.

The manner in which the compounds of formula I can be prepared is illustrated by reference to Scheme A. The compounds of formula I are obtained from the corresponding compound of formula III. $R_1$ represents all of the same groups enumerated earlier except those groups which contain a primary or secondary amino group. When $R_1$ contain a primary or secondary amino group, this is a special case which will be discussed hereinafter.

Scheme A

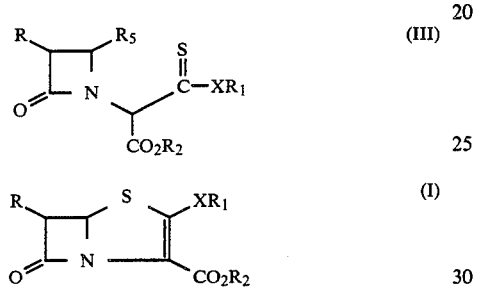

The compounds of formula I are obtained by cyclization of the corresponding compound of formula III as shown in Scheme A. The cyclization is normally carried out by treatment of the compound of formula III with a base, for example, an excess, e.g. a ten-fold excess, of a trialkyl amine wherein each alkyl has 1-4 carbon atoms, such as triethylamine or diisopropylethylamine, or a tetraalkylammonium hydroxide wherein each alkyl has 1-4 carbon atoms, e.g., diisopropylethylamine in a reaction-inert solvent such as chloroform, tetrahydrofuran, or dichloromethane. The reaction is normally carried out at a temperature range of about 0° to 40° C., preferably about 25° C. and it is normally complete within a few hours, e.g. from 2 to 24 hours. At the end of the cyclization reaction, the amine hydrochloride is removed by washing with water, and the product is recovered by, for example, solvent evaporation.

The manner in which the compounds of formula III are obtained is illustrated by reference to Scheme B. According to the invention, these compounds are obtained by halogenation of a compound of the formula VII. For example, chlorination of a compound of formula VII where i is zero normally carried out by treating the compound with one molar equivalent or more of chlorine in a chlorinated hydrocarbon solvent such as dichloromethane, chloroform or carbon tetrachloride, at a temperature range of about −40° to 5° C., preferably about −20° C. The reaction is normally complete within one to two hours, and then the product is recovered by solvent evaporation. The chloro compound III is usually obtained as an oil, which is usually used directly, without purification, in the preparation of a compound of formula I.

Other suitable chlorinating reagents may also be employed. Furthermore $R_5$ need not be chloro in order for the conversion of III to I to occur. Other halogens, e.g., bromo may be employed. These other halogens may be prepared by appropriate halogenation of VII; for example, bromination with bromine. Of course, $R_5$ may be any other suitable leaving group which will allow cyclization of III to occur.

SCHEME B

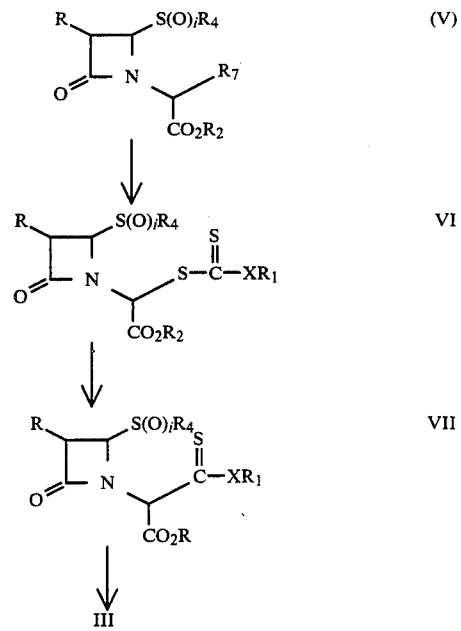

The compounds of formula VII are obtained by desulfurization of a xanthate or trithiocarbonate of formula VI. The desulfurization is normally carried out by treating the compound of formula VI with about one molar equivalent of a strong base such as sodium hydride in a reaction-inert solvent such as tetrahydrofuran, at a temperature of between about −10° and 5° C., preferably about 0° C. The reaction is normally complete within about one to two hours, and then the reaction is quenched by the addition of about one molar equivalent of acetic acid. The product is then recovered by solvent evaporation. Although the product thus obtained can be used directly in the preparation of a compound of formula III, it is usual to purify VII. Purification can be achieved by standard techniques; a particularly convenient method is chromatography on silica gel.

In most instances, in the conversion of a compound of the formula VI into a compound of formula VII, it is advantageous to add one molar equivalent of a trivalent phosphorus compound such as a trialkylphosphine (e.g., tributylphosphine, tricyclohexylphosphine), a triarylphosphine (e.g., triphenylphosphine) or a trialkylphosphite (e.g., trimethylphosphite, triethylphosphite), preferably triphenylphosphine, to the reaction medium prior to the addition of the strong base.

The compounds of formula VI are obtained by coupling the compound of the formula V with a xanthate salt of the formula $M^+R_1$—O—(C=S)—S$^-$, or a trithiocarbonate salt of the formula $M^+R_1$—S—(C=S)—S$^-$, wherein $M^+$ represents a metal cation such as sodium or potassium. The coupling is normally carried out by contacting equimolar amounts of the xanthate salt or trithiocarbonate salt and the compound of the formula V in a biphasic organic-aqueous mixture such as dichloromethane and water, in the presence of one molar equivalent or less of a phase-transfer catalyst such as benzyltriethylammonium chloride. The reaction is normally carried out at a temperature between about 0° and 30° C., preferably about 0° C., and it is usually complete within one to two hours. At the completion of the reaction, the product is in the organic phase, and it can be recovered by separating the layers and evaporating the solvent. The product can be purified by conventional methods for a beta-lactam compound, e.g. chromatography using silica gel.

The method by which the compound of formula V can be prepared is shown in Scheme C. Thus, it will be seen that the compound of formula V is prepared by halogenation of the corresponding hydroxy compound (XIII) with a halogenating agent such as thionyl chloride, methanesulfonyl chloride or methanesulfonyl bromide. For thionyl chloride, the chlorination is carried out by treating a solution of the compound of formula XIII in tetrahydrofuran with a slight molar excess of thionyl chloride, in the presence of a hindered amine such as 2,6-lutidine, at about 0° C. Reaction takes place rapidly, and after about 15 minutes, the product is recovered by evaporation of the filtered tetrahydrofuran solution.

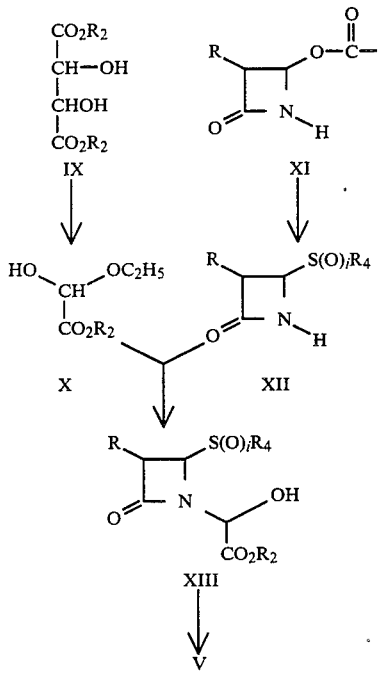

SCHEME C

The compound of formula XIII is prepared by coupling a compound of formula XII with the ester of glyoxylic acid ethyl hemiacetal (X). The coupling is carried out by heating the two reagents in refluxing benzene, with provision for continuous removal of water and ethanol by azeotropic distillation.

An alternate procedure is to treat XII (R is preferably 1-hydroxyethyl or hydroxymethyl having a hydroxyl-protecting group such as p-nitrobenzyloxycarbonyl) with a benzyloxycarbonylformaldehyde hydrate or hemiacetal to obtain XIII (R$_2$=a benzyl group). The preferred benzyloxycarbonylformaldehyde hydrate is p-nitro-benzyloxycarbonyl-formaldehyde hydrate which is reacted with XII in an aprotic solvent such as benzene or dimethylformamide, preferably benzene at a temperature of about 80° C.

The azetidine of formula XII is prepared from the corresponding 4-acetoxy-2-oxo-azetidine XI by reaction with the sodium salt of the thiol, and the ester of glyoxylic acid ethyl hemiacetal X is prepared by periodic acid cleavage of the corresponding ester of tartaric acid IX. 4-Acetoxy-2-oxo-azetidines XI and the tartrates IX are prepared by methods known in the art. The sulfide (XII or XIII, i is zero) may be oxidized to the sulfoxide (i is one) with an oxidizing agent such as soidum periodate, ozone or, preferably, m-chloroperbenzoic acid. Oxidation with m-chloroperbenzoic acid is generally carried out with a reaction-inert solvent such as dichloromethane at a temperature between about −30° and 0° C., preferably about −20° C.

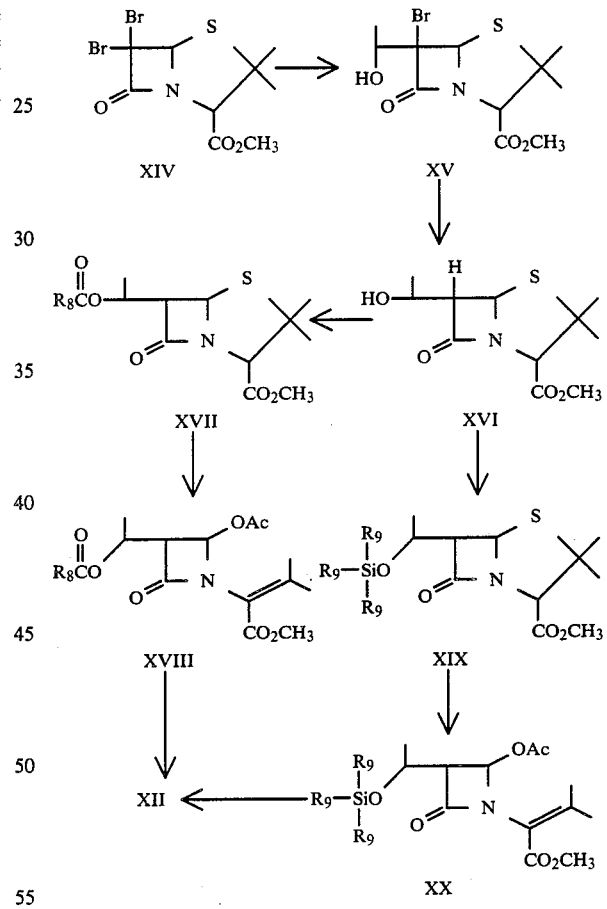

SCHEME D

When R is 1-hydroxyalkyl or the hydroxy protected group thereof, the compound of formula XII can be prepared according to Scheme D from the known dibromo penam of formula XIV. The dibromo penam (XIV) undergoes an exchange reaction with t-butyl magnesium chloride at a temperature of between about −90° and −40° C., preferably about −76° C. in a reaction-inert solvent such as tetrahydrofuran, diethyl ether or toluene preferably tetrahydrofuran. Other organometallic reagents may also be employed. The resultant reaction mixture is treated in situ with the appropriate aldehyde; acetaldehyde for the 1-hydroxyethyl derivative, formaldehyde for the hydroxymethyl derivative. The aldehyde is added at between about −80° and −60° C., preferably about −76° C. for acetaldehyde.

The resulting bromo hydroxy penam XV is hydrogenated to remove the 6-bromo substituent. Preferred hydrogenation catalysts include noble metals such as platinum and palladium. A suitable hydrogenation catalyst is palladium on calcium carbonate. The reaction is carried out in a protic medium such as 1:1 methanol-water or water-tetrahydrofuran preferably 1:1 methanol-water at a pressure of about 1 to 4 atm., preferably 4 atm. and a temperature of between about 0° and 30° C., preferably about 25° C.

The hydrogenated compound XVI is treated to protect the hydroxyl with a hydroxyl-protecting group, for example, a protecting group of the formula $R_8CO$, such as benzyloxycarbonyl, p-nitrobenzyloxycarbonyl, allyloxycarbonyl, 2,2,2-trichloroethoxycarbonyl and the like. The hydroxyl is reacted, for example, with the corresponding chloride, bromide or iodide of the hydroxyl-protecting group. For, p-nitrobenzyloxycarbonyl, the chloride is reacted with XVI in a suitable reaction-inert solvent such as dichloromethane at a temperature between about 0° and 30° C., preferably about 25° C.

The resulting alkanoyl penam XVII is treated with mercuric acetate in acetic acid at a temperature of about 90° C. to yield the olefin XVIII.

In order to obtain the desired azetidine XII, the olefin XVIII is ozonized in a reaction insert solvent such as dichloromethane at a temperature of between about −80° and −40° C., preferably about −76° C. The reaction product is not isolated, but is treated with an alkanol such as methanol to yield the azetidine XII.

Alternatively the alcohol of formula XVI can be protected with a trialkylhalosilane of formula

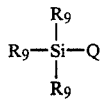

wherein $R_9$ at each occurrence is independently an alkyl of 1-6 carbon atoms and Q is chloro, bromo or iodo. Thus, dimethyl-t-butylchlorosilane in the presence of an amine proton acceptor such as imidazole in a polar, aprotic solvent such as dimethylformamide a temperature range of between about 5° and 40° C., preferably about 25° C. forms a trialkylsilyl hydroxyl-protecting group as shown in formula XIX.

Mercuric acetate treatment XIX under the conditions employed with XVII results in the olefin XX. Ozonolysis of this olefin XX in the same method employed with XVIII results in XII wherein R is the trialkylsilyl derivative of 1-hydroxylethyl or hydroxymethyl.

The xanthate salts of the formula $M^+R_1$—O—(C=S)—$S^-$ are prepared from the appropriate alcohol of formula $R_1$—OH and carbon disulfide in the presence of a strong base. For example, the alcohol of formula $R_1$—OH is reacted with an equimolar amount of sodium hydride or potassium t-butoxide, followed by a slight excess of carbon disulfide, according to well-known procedures.

The trithiocarbonate salts of the formula $M^+R_1$—S—(C=S)—$S^-$ are similarly prepared by the procedure employed to prepare the xanthate salts, from the appropriate mercaptan of the formula $R_1$—SH.

Conversion of a compound of formula I wherein $R_2$ is an acid protecting group into a compound of formula I wherein $R_2$ is hydrogen can be performed by employing known methods. For example, when $R_2$ is benzyl or p-nitrobenzyl the preferred method is a conventional hydrogenolysis reaction, and it is carried out in conventional fashion for this type of transformation. Thus, a solution of a compound of the formula I ($R_2$ is an acid protecting group) is stirred or shaken under an atmosphere of hydrogen, or hydrogen mixed with an inert diluent such as nitrogen or argon, in the presence of a catalytic amount of a hydrogenolysis catalyst, for example, a noble metal catalyst such as palladium-on-calcium carbonate. Convenient solvents for this hydrogenolysis are lower-alkanols, such as methanol; ethers, such as tetrahydrofuran and dioxan; low molecular weight esters, such as ethyl acetate and butyl acetate; water; and mixtures of these solvents. However, it is usual to choose conditions under which the starting material is soluble. The hydrogenolysis is usually carried out at about 25° C. and at a pressure from about 0.5 to about 5 $kg/cm^2$. The catalyst is usually present in an amount from about 10 percent by weight based on the starting material up to an amount equal in weight to the starting material, although larger amounts can be used. The reaction commonly takes about one hour, after which the compound of the formula I ($R_2$ is hydrogen), is recovered simply by filtration followed by removal of the solvent in vacuo. If palladium-on-calcium carbonate is used as the catalyst, the product is often isolated as the calcium salt. The compounds of formula I can be purified by conventional methods for beta-lactam compounds. For example, the compounds for formual I can be purified by gel filtration on Sephadex, or by recrystallization.

If for I, $R_1$ is 1-hydroxyethyl or hydroxymethyl protected with benzyl derivatives such as p-nitrobenzyloxycarbonyl, the hydroxyl-protecting group can be removed using the hydrogenolysis procedure just described.

For compounds of formula I wherein R is 1-hydroxyethyl or hydroxymethyl whose hydroxyl group is protected with a trialkylsilyl group, the trialkylsilyl group is preferably removed prior to the hydrogenolysis to remove the acid-protecting group (I, $R_2$ is an acid protecting group). The trialkylsilyl group can be removed with a tetralkylammonium fluoride generally wherein each alkyl has 1-7 carbon atoms an ethereal solvent such as tetrahydrofuran at about 25° C.

The compound of the formula I, wherein $R_1$ includes a primary amino group, can be prepared from the corresponding azido compound by hydrogenolysis. The conditions described earlier for removal from I of $R_2$ wherein $R_2$ is an acid protecting group such as the p-nitrobenzyl group can be used for this azido hydrogenolysis reaction, but it is necessary to allow the reaction to proceed until reaction with hydrogen ceases. Thus, it is evident that if one subjects the compound of formula I, wherein $R_1$ includes an azido group, to the aforesaid hydrogenolysis conditions, partial hydrogenolysis leads to the compound of formula I, wherein $R_1$ includes the azido group; exhaustive hydrogenolysis leads to the compound of formula I, wherein the azido group of $R_1$ has been converted to a primary amino group.

Alternatively, primary or secondary amines can be protected with suitable amine-protecting groups. A particularly advantageous class of amine-protecting groups are benzyloxycarbonyls such as benzyloxycarbonyl or p-nitrobenzyloxy-carbonyl, allyloxycarbonyl, 2,2,2-trichloroethoxycarbonyl and the like. The corresponding benzyloxycarbonyl chloride or bromide, for example p-nitrobenzyloxycarbonyl chloride, can be reacted with the amine in a reaction-inert solvent such as dichloromethane in the present of a tertiary amine at a temperature range of about −20° to 25° C., preferably about 0° C. The amine-protecting group, such as p-nitrobenzyloxy-carbonyl, can be removed by the same hydrogenolysis procedure previously described.

The compounds of formula I are acidic and will form salts with basic agents. Such salts are considered to be within the scope of this invention. These salts can be prepared by standard techniques, such as contacting the acidic and basic components, usually in a stoichiometric ratio, in an aqueous, non-aqueous or partially aqueous medium, as appropriate. They are then recovered by filtration, by precipitation with a non-solvent followed by filtration, by evaporation of the solvent, or in the case of aqueous solutions by lyophilization, as appropriate. Basic agents which are suitably employed in salt formation belong to both the organic and inorganic types, and they include ammonia, organic amines, alkali metal hydroxides, carbonates, bicarbonates, hydrides and alkoxides, as well as alkaline earth metal hydroxides, carbonates, hydrides and alkoxides. Representative examples of such bases are primary amines, such as n-propylamine, n-butylamine, aniline, cyclohexylamine, benzylamine and octylamine; secondary amines, such as diethylamine, morpholine, pyrrolidine and piperidine; tertiary amines, such as triethylamine, N-ethylpiperidine, N-methylmorpholine and 1,5-diazabicyclo[4,3,0]-non-5-ene; hydroxides, such as sodium hydroxide, potassium hydroxide, ammonium hydroxide and barium hydroxide; alkoxides, such as sodium ethoxide and potassium ethoxide; hydrides, such as calcium hydride and sodium hydride; carbonates, such as potassium carbonate and sodium carbonate; bicarbonates, such as sodium bicarbonate and potassium bicarbonate; and alkali metal salts of long-chain fatty acids, such as sodium 2-ethyl-hexanoate.

Preferred salts of the compounds of the formula are sodium, potassium and calcium salts.

As indicated hereinbefore, the compounds of formula I and salts thereof are anti-bacterial agents. The in vitro activity of the compounds of the formula I and salts thereof can be demonstrated by measuring their minimum inhibitory concentrations (MIC's) in mcg./ml. against a variety of microorganisms. The procedure which is followed is the one recommended by the International Collaborative Study on Antibiotic Sensitivity Testing (Ericcson and Sherris, *Acta. Pathologica et Microbiologia Scandinav*, Supp. 217, Section B: 64–68 [1971]), and employs brain heart infusion (BHI) agar and the inocula replicating device. Overnight growth tubes are diluted 100 fold for use as the standard inoculum (20,000–10,000 cells in approximately 0.002 ml. are placed on the agar surface; 20 ml. of BHI agar/dish). Twelve 2 fold dilutions of the test compound are employed, with initial concentration of the test drug being 200 mcg./ml. Single colonies are disregarded when reading plates after 18 hrs. at 37° C. The susceptibility (MIC) of the test organism is accepted as the lowest concentration of compound capable of producing complete inhibition of growth as judged by the naked eye.

The following Examples and Preparations are provided solely for further illustration. Infra-red (IR) spectra were measured either as potassium bromide discs (KBr disc), or as solutions in chloroform (CHCl$_3$), methylene chloride (CH$_2$Cl$_2$) or dimethyl sulfoxide (DMSO), and diagnostic absorption bands are reported either in wave numbers (cm$^{-1}$) or in microns (micrometers). Nuclear magnetic resonance (NMR) spectra were measured for solutions in deuterochloroform (CDCl$_3$) perdeutero-water (D$_2$O) or perdeuterodimethyl sulfoxide (DMSO-d$_6$), or mixtures thereof, and peak positions are expressed in parts per million downfield from tetramethylsilane. The following abbreviations for peak shapes are used: s, singlet; d, doublet; t, triplet; q, quartet; m, multiplet c, complex; b, broad. The abbreviations "ss" and "sss" denote that a particular proton appeared as two or three singlets respectively, owing to the presence of diastereoisomers. Throughout the Examples and Preparations, the abbreviation "PNB" represents the p-nitrobenzyl group.

EXAMPLE 1 p-Nitrobenzyl 2-(4-ethylthio-3-p-nitrobenzyloxycarbonyloxyethyl-2-oxo-1-azetidinyl)-2-(1,3-dioxan-5-yl-oxythiocarbonyl)acetate A solution of 8.40 g p-nitrobenzyl 2-(4-ethylthio-3-p-nitrobenzyloxycarbonyloxyethyl-2-oxo-1-azetidinyl)-2-(1,3-dioxan-5-yl-oxythiocarbonylthio)acetate and 2.95 g triphenylphosphine in 200 ml anhydrous tetrahydrofuran was cooled to 0° C. under a nitrogen atmosphere, sodium hydride (550 mg. 50% oil dispersion) was added and the reaction mixture was stirred at 0° C. for 20 min. Acetic acid (0.65 ml) was then added dropwise at 0° C. and the resulting solution was concentrated in vacuo. The residue was dissolved in 200 ml ethyl acetate and the solution was washed successively with 100 ml saturated aqueous sodium bicarbonate solution and 100 ml water, dried over anhydrous sodium sulfate and concentrated in vacuo. The residue was chromatographed on silica gel eluting with 15% ethyl acetate in chloroform to yield 6.9 g of the title compound. The NMR spectrum in deuterochloroform showed absorptions at 1.0–1.56 (c, 6H); 2.58 (m, 2H); 3.4 (m, 1H); 3.86–4.1 (c, 5H); 4.63–5.46 (c, 9H); 7.5 (m, 4H) and 8.2 (m, 4H) ppm.

EXAMPLE 2

The compounds of formula VII wherein R is p-nitrobenzyloxycarbonyloxyethyl, X is oxygen, R$_4$ is ethyl, i is zero and R$_2$ is p-nitrobenzyl as listed for different R$_1$ in Table I were obtained by the desulfurization of the corresponding xanthate of formula VI, using the procedure of Example 1. For the compounds in Table I, NMR spectra were measured for deuterochloroform solutions.

TABLE I

| R$_1$ | NMR (ppm) |
|---|---|
| 2-piperidinon-5-yl | 1.0–1.56 (c,6H); 2.0–2.72 (c,6H); 3.36 (m,1H); 3.58 (c,2H); 4.8–5.32 (c,8H); 6.1 (b,1H); 7.48 (m,4H); 8.2 (m,4H) |
| 1-formyl-3-piperidyl (IR: 5.64, 5.70 5.97 microns (CHCl$_3$)) | 1.0–2.2 (c,10H); 2.6 (m,2H); 3.1–4.1 (c,5H); 4.95–5.4 (c,7H); 5.5 (m,1H); 7.5 (m,4H); |
| 1-methoxy-2-propyl | 1.04–1.6 (c,9H); 2.6 (m,2H); 3.3(s) and 3.26–3.6 (c,6H); 4.96–5.4 (c,7H); 5.66 (c,1H); 7.5 (m,4H); and 8.2 (m,4H) |
| 1,3-dioxolan-2-yl-methyl | 1.0–1.58 (c,6H); 2.6 (m,2H); 3.4 (m,1H); |

TABLE I-continued

| $R_1$ | NMR (ppm) |
|---|---|
| | 3.98 (b,4H); 4.5 (d, 2H); 4.9–5.44 (c,8H); 7.52 (m,4H); and 8.2 (m,4H) |
| 2-pyrrolidinon-3-yl | 0.98–1.66 (c,6H); 2.26–3.0 (c,4H); 3.0–3.5b (c,3H); 4.75–5.46 (c,8H); 5.9 (b,1H); 7.5 (m,4H); and 8.2 (m,4H) |
| 3-methyl-1,3-oxazolidin-2-on-4-ylmethyl | 1.0–1.56 (c,6H); 2.54 (m,2H); 2.86 (s,3H); 3.4 (m,1H); 3.9–5.42 (c,12H); 7.5 (m,4H); and 8.2 (m,4H) |
| 1,3-dioxolan-4-ylmethyl | 1.02–1.68 (c,6H); 2.58 (m,2H); 3.42 (m,1H); 3.6–4.66 (c,5H); 4.68–5.4 (c,9H); 7.54 (m,4H); and 8.2 (m,4H) |
| 2-methoxyethyl | 1.06–1.58 (c,6H); 2.6 (m,2H); 3.36 (s) and 3.26–3.8 (c,6H); 4.54–5.4 (c,8H); 6.52 (s,1H); 7.5 (m,4H); and 8.2 (m,4H) |

TABLE II

| $R_1$ | IR (microns) | NMR (ppm) |
|---|---|---|
| 2-methoxyethyl | 5.56 | 1.2 (t,3H); 2.36–3.86 (m,9H); 4.7 (m,2H); 5.1 (m,1H); 5.25, 5.35 and 5.4 (sss,3H); 7.55 (d,2H); 8.25 (d,2H) |
| 2-phenoxyethyl | 5.66 | 1.15 (m,3H); 2.34–3.62 (m,4H); 4.24 (m,2H); 4.7–5.2 (m,3H); 5.24 (s,2H); 5.34 and 5.48 (ss,1H); 6.7–7.68 (m,7H); 8.14 (d,2H) |
| 2-thiophenoxyethyl | 5.66 | 1.0–1.4 (m,3H); 2.3–3.9 (m,6H); 4.45–5.35 (m,6H); 7.1–7.62 (m,7H); 8.16 (d,2H) |
| 2-phenylethyl | 5.66 | 1.2 (t,3H); 2.3–3.65 (m,6H); 4.6–5.14 (m,3H); 5.28 and 5.32 (ss,3H); 7.15–7.65 (m,7H); 8.22 (d,2H) |
| 2-azidoethyl | 4.77 5.66 | 1.22 (t,3H); 2.4–3.86 (m,6H); 4.62–5.25 (m,3H); 5.3 and 5.4 (ss,3H); 7.58 (d,2H); 8.25 (d,2H) |

EXAMPLE 3 p-Nitrobenzyl 2-(4-Ethylthio-2-oxo-1-azetidinyl)-2-(ethoxythiocarbonyl)acetate

To a stirred solution of 3.5 g. of p-nitrobenzyl 2-(4-ethylthio-2-oxo-1-azetidinyl)-2-(ethoxythiocarbonylthio)acetate in 100 ml of tetrahydrofuran, at 0° C., was added 545 mg. of a 50% dispersion of sodium hydride in mineral oil. Stirring was continued at 0°–5° C. for 1 hour, and then a solution of 713 mg. of acetic acid in 5 ml. of tetrahydrofuran was added dropwise. The reaction mixture was concentrated to dryness in vacuo, and the residue was partitioned between a mixture of 100 ml. of chloroform and 50 ml of dilute hydrochloric acid. The chloroform layer was removed and washed successively with 50 ml. of water, 50 ml. of saturated sodium bicarbonate and 50 ml. of water. The chloroform solution was dried using anhydrous sodium sulfate. Evaporation in vacuo gave the title compound as a yellow viscous liquid. This product was purified by chromatography on silica gel (150 g.), eluting with a 95:5 mixture of chloroform:ethyl acetate. The product containing fractions were combined and evaporated in vacuo to give 1.8 g. of the title compound as a yellow liquid. The IR spectrum chloroform of the product showed an absorption at 5.56 microns. The NMR spectrum deuterochloroform showed absorptions at 1.0–1.6 (m, 6H); 2.35–3.68 (m, 4H); 4.6 (q, 2H); 5.1 (m, 1H); 5.2 and 5.3 (ss, 3H); 7.46 (d, 2H); and 8.3 (d, 2H) ppm.

EXAMPLE 4

The compounds of formula VII wherein R is hydrogen, X is oxygen, $R_4$ is ethyl, i is zero, and $R_2$ is p-nitrobenzyl as listed for different $R_1$ in Table II were obtained by desulfurization of the appropriate xanthate of formula VI, using the procedure of Example 3. For the compounds in Table I, IR spectra were measured for solutions in chloroform and NMR spectra were measured for solutions in deuterochloroform.

EXAMPLE 5 p-Nitrobenzyl 2-(4-Ethylthio-2-oxo-1-azetidinyl)-2-(2-acetamidoethoxythiocarbonyl)acetate To a stirred solution of 1.02 g. of p-nitrobenzyl 2-(ethylthio-2-oxo-1-azetidinyl)-2-(2-acetamidoethoxythiocarbonylthio)acetate and 514 mg. of triphenylphosphine in 25 ml. of tetrahydrofuran, at ca. 0° C., was added 101 mg. of a 50% dispersion of sodium hydride in mineral oil. Stirring was continued for 1 hour at ca. 0° C., and then 0.14 ml. of acetic acid was added. The resulting solution was evaporated in vacuo, and then the residue was dissolved in 50 ml. of chloroform. The chloroform solution was washed with water, dried with anhydrous sodium sulfate, and evaporated in vacuo to give a solid residue (1.58 g.). The solid was chromatographed on 100 g. of silica gel eluting with a 95:5 mixture of ethyl acetate:methanol. The fractions containing the product were combined and evaporated in vacuo to give 500 mg. of the title compound. The IR spectrum in chloroform showed absorptions at 5.66 and 5.98 microns. The NMR spectrum in deuterochloroform showed absorptions at 1.2 (m, 3H); 2.0 (s, 3H); 2.4 3.9 (m, 6H); 4.7 (m, 2H); 5.13 (m, 1H); 5.28, 5.36 and 5.44 (sss, 3H); 7.0 (m, 1H); 7.64 (d, 2H); and 8.3 (d, 2H) ppm.

EXAMPLE 6

The compounds of formula VII where R is hydrogen, X is oxygen, $R_4$ is ethyl, i is zero and $R_2$ is p-nitrobenzyl as listed for different $R_1$ in Table III were obtained by desulfurization of the appropriate xanthate of formula VI, using the procedure of Example 5. For the compounds in Table III, IR spectra were measured for solutions in chloroform unless otherwise indicated and NMR spectra were measured for solutions in deuterochloroform unless otherwise indicated.

TABLE III

| $R_1$ | IR microns | NMR (ppm) |
|---|---|---|
| 2-ethoxyethyl | 5.63 | 1.08–1.45 (m,6H); 2.4– |

TABLE III-continued

| R₁ | IR microns | NMR (ppm) |
|---|---|---|
| | | 3.95 (m,8H); 4.58 (m,2H); 5.17 (m,1H); 5.27, 5.38 and 5.43 (sss,3H); 7.58 (d,2H); 8.26 (d,2H) |
| 2-(2-(methoxy)-ethoxy)ethyl | 5.63 | 1.22 (t,3H); 2.38–4.0 (m,13H); 4.7 (m,2H); 5.12 (m,1H); 5.25, 5.36, 5.42 (s,3H); 7.58 (d,2H); 8.22 (d,2H) |
| 2-(morpholino)ethyl | 5.64 | 1.2 (t,3H); 2.32–3.8 (m,14H); 4.62 (t,2H); 5.1 (m,1H); 5.2 and 5.3 (s,3H); 7.52 (d,2H); 8.22 (d,2H) |
| 2-(2-thienyl)ethyl | 5.64 | 1.16 (t,3H); 2.3–3.6 (m,6H); 4.5–5.16 (m,3H); 5.2, 5.24 and 5.28 (sss,3H); 6.8–7.68 (m,5H); 8.2 (d,2H) |
| 2-(2-pyridyl)ethyl | 5.66 | 1.18 (t,3H); 2.3–3.6 (m,6H); 4.7–5.18 (m,3H); 5.2 and 5.25 (ss,3H); 6.96–7.85 (m,5H); 8.2 (d,2H); 8.5 (m,1H) |
| 2-(1-pyrazolyl)-ethyl | 5.62 | 1.18 (m,3H); 2.3–3.68 (m,4H); 4.36–5.12 (m,5H); 5.2 and 5.26 (ss,3H); 6.22 (m,1H); 7.34–7.7 (m,4H); 8.2 (d,2H) |
| 2-(4-methyl-5-thiazolyl)ethyl | 5.63 | 1.2 (t,3H); 2.3–3.7 (m,9H); 4.7 (m,2H); 4.96–5.38 (m,4H); 7.72 (d,2H); 8.22 (d,2H); 8.62 (s,1H) |
| 2-(2-oxo-1-imidazolidinyl)ethyl | 5.66 5.88 | 1.22 (m,3H); 2.38–3.78 (m,10H); 4.62 (m,2H); 5.12 (m,1H); 5.26 and 5.36 (ss,3H); 7.6 (d,2H); 8.28 (d,2H) |
| 2-(2-oxo-1-pyrrolidinyl)ethyl | 5.65 | 1.2 (m,3H); 1.7–3.8 (m,12H); 4.62 (m,2H); 5.1 (m,1H); 5.2, 5.25 and 5.3 (sss,3H); 7.56 (d,2H); 8.22 (d,2H) |
| 2-(2-thiazolylthio)ethyl | 5.66 | 1.02–1.4 (m,3H); 2.35–3.74 (m,6H); 4.66–5.4 (m,6H); 7.36–7.7 (m,4H); 8.2 (d,2H) |
| 2-methoxycyclopentyl | 5.66 | 1.0–1.4 (m,3H); 1.6–2.0 (m,6H); 2.0–4.0 (m,5H); 3.3 (s,3H); 5.2 (m,1H); 5.3 (m,2H); 5.6 (m,1H); 7.5 (d,2H); 8.2 (d,2H) |
| 2-methoxycyclohexyl | 5.65 | 1.0–2.2 (m,11H); 2.2–4.0 (m,5H); 3.4 (s,3H); 5.0 (m,1H); 5.4 (d,2H); 5.5 (m,1H); 7.5 (d,2H); 8.2 (d,2H) |
| 2-azidocyclohexyl | 4.76 5.66 | 1.0–2.0 (m,11H); 2.0–4.0 (m,5H); 5.2 (m,1H); 5.3 (d,2H); 5.4 (m,1H); 7.5 (d,2H); 8.2 (d,2H) |
| 2-azidocyclopentyl | 4.76 5.63 | 1.0–1.4 (m,3H); 1.6–2.0 (m,6H); 2.2–3.8 (m,4H); 4.1 (m,1H); 5.2 (m,1H); 5.3 (s,2H); 5.4 (m,1H); 7.5 (d,2H); 8.2 (d,2H) |
| 3-tetrahydrofuranyl | 5.65 | 1.0–1.4 (t,3H); 2.0–3.8 (m,6H); 3.8–4.1 (m,4H); 5.0 (m,1H); 5.3 (s,2H); 6.9 (m,1H); 7.8 (d,2H); 8.2 (d,2H) |
| 1-acetyl-2-pyrroli-dinyl | 5.65 | 1.0–1.4 (m,5H); 2.0 (s,3H); 2.2–4.0 (m,8H); 5.2 (m,1H); 5.4 (s,2H); 5.9 (m,1H); 7.6 (d,2H); 8.2 (d,2H) |
| 1-acetyl-3-piperi-dinyl | 5.66 | 1.0–1.4 (m,3H); 1.9–2.0 (m,4H); 2.0 (s,3H); 2.2–4.0 (m,8H); 5.2 (m,1H); 5.3 (s,2H); 5.6 (m,1H); 7.5 (d,2H); 8.2 (d,2H) |
| 2-tetrahydrofuranyl-methyl | 5.65 | 1.0–2.4 (m,3H); 1.6–2.1 (m,4H); 2.2–3.8 (m,4H); 3.8–4.1 (m,3H); 4.6 (d,2H); 5.2 (m,1H); 5.4 (s,2H); 7.6 (d,2H); 8.2 (d,2H) |
| 2-(2-pyridinoylamino-ethyl | 5.64 5.98 | 1.15 (m,3H); 2.5 (q,2H); 2.8–4.05 (c,4H); 4.7 (m,2H); 4.92–5.35 (c,4H); 7.2–8.7 (c,9H). |
| 1-formyl-3-piperidyl | 5.64 5.72 | 1.03 (t,3H); 1.44–2.26 (c,4H); 2.38–4.1 (c,8H); 4.7–5.7 (c,5H); 7.56 (d,2H); 7.82–8.36 (c,3H). |
| N—methylaminocarbonyl-methyl | 5.68 5.98 | 1.2 (m,3H); 2.6 (q), 2.76 (d) and 2.16–3.7 (c,7H); 4.8–5.44 (c,6H); 7.56 (c,3H); 8.2 (d,2H). |
| 1-(aminocarbonyl)ethyl | 5.67 5.92 (CH₂Cl₂) | 1.07–1.7 (c,6H); 2.32–3.84 (c,4H); 4.74–5.4 (c,4H); 5.7 (q,1H); 6.14 (b,1H); 7.13 (b,1H); 7.48 (d,2H); 8.15 (d,2H) |
| 2-(methoxymethylcar-bonyl-amino)ethyl | 5.66 5.96 (CH₂Cl₂) | 1.26 (m,3H); 2.66 (q, 2H); 2.9–4.1 (c, total 9H) including 3.45 (s,3H), 3.76 (q,2H), 3.9 (s,2H); 4.7 (m,2H); 5.14 (m,1H); 5.3 (d,1H); 5.4 (s,2H); 7.1 (b,1H); 7.6 (d,2H); 8.2 (d,2H). |
| 2-(aminocarbonyloxy)ethyl | 5.65 5.76 (CH₂Cl₂) | 1.18 (m,3H); 2.58 (m,2H); 2.8–5.1 (c, 8H); 5.2 (d,1H); 5.3 (s,2H); 7.55 (m,2H); 8.2 (d,2H). |
| 1,3-dimethoxy-2-propyl | 5.65 | 1.25 (m,3H); 2.5 (m,2H); 2.84–3.9 (c,12H) including 3.35 (5,6H); 4.9–5.46 (c, 4H); 5.8 (m,1H); 7.6 (d,2H); 8.28 (d,2H). |
| 2-(2-furylcarbonyl-amino)ethyl | 5.64 6.0 (CH₂Cl₂) | 1.25 (m,3H); 2.6 (q,2H); 2.8–4.0 (C,4H); 4.74 (m,2H); 5.08 (m,1H); 5.24 (d,1H); 5.34 (s,2H); 6.5 (m,1H); 7.0 (b,1H); 7.1 (d,1H); 7.42 (d,1H); 7.5 (d,2H); 8.2 (d,2H). |
| 1,3-dioxan-5-yl | 5.62 | 1.2 (t,3H); 2.33–3.5 (c,4H); 4.04 (m,4H); 4.66–5.44 (c,7H); 7.5 (m,2H); 8.2 (d,2H). |
| 1-methyl-2-piperidinon-3-yl | 5.66 6.04 | 1.22 (m,3H); 1.7–2.2 (c,4H); 2.6 (m,2H); 2.96 (5,3H); 3.0–3.65 (c,4H); 4.8–5.46 (c,4H); 5.86 (m,1H); 7.56 (d,2H); 8.2 (d,2H). |
| 1-(aminocarbonylmethyl-2-piperidnon-3-yl | 5.68 6.0 | 1.2 (m,3H); 1.7–4.4 (c,12H); 4.8–5.4 (c,5H); 6.0 (n,2H); 7.5 (m,2H); 8.2 (d,2H). |
| 2-(2-acetylamino-ethoxy)ethyl | 5.68 6.0 (CH₂Cl₂) | 1.25 (m,3H); 2.0 (s,3H); 2.6 (m,2H); 2.8–4.0 (c,8H); 4.62 (m,2H); 4.95–5.4 (c,4H); 6.44 (b,1H); |

TABLE III-continued

| R₁ | IR microns | NMR (ppm) |
|---|---|---|
|  |  | 7.52 (d,2H); 8.2 (d,2H). |
| 2-piperidinon-3-yl | 5.68 | 1.2 (m,3H); 1.6–3.66 |
|  | 5.98 | (c,8H); 4.8–5.4 (c,5H); |
|  |  | 6.4 (b,1H); 7.5 (d,2H); |
|  |  | 8.2 (d,2H). |
| 2-pyrrolidinon-3-yl | 5.66 | 1.2 (m,3H); 2.36–3.8 |
|  | 5.85 | (c,8H); 4.9–5.5 (c,5H); |
|  |  | 7.6 (c,3H); 8.2 (m,2H) |
|  |  | (DMSO-d₆). |
| 2-piperidinon-5-yl | 5.64 | 1.24 (m,3H); 2.0–3.8 |
|  | 6.0 | (c,11H); 5.05 (m,1H); |
|  |  | 5.2 (m,1H); 5.3 (5,2H); |
|  |  | 7.2 (b,1H); 7.5 (d,2H); |
|  |  | 8.2 (d,2H). |
| 3-methyl-1,3-oxazolid-2-on-4-ylmethyl | 5.66 | 1.24 (m,3H); 2.6 (q,2H); |
|  |  | 2.9 (s,3H); 3.1–4.8 |
|  |  | (c,7H); 5.0 (m,1H); |
|  |  | 5.22 (m,1H); 5.35 (s,2H); |
|  |  | 7.5 (d,2H); 8.2 (d,2H). |
| 1,3-dioxolan-4-ylmethyl | 5.64 (CH₂Cl₂) | 1.24 (m,3H); 2.6 (m,2H); |
|  |  | 2.82–4.6 (c,7H); 4.9 |
|  |  | (d,2H); 5.1 (m,1H); 5.24 |
|  |  | (d,1H); 5.34 (s,2H); 7.56 |
|  |  | (d,2H); 8.22 (d,2H). |

EXAMPLE 7 p-Nitrobenzyl 2-(4-chloro-3-p-nitrobenzyloxycarbonyloxyethyl-2-oxo-1-azetidinyl)-2-(1,3-dioxan-5-yl-oxythiocarbonyl)-acetate A solution of 6.90 g of p-nitrobenzyl 2-(4-ethylthio-3-p-nitrobenzyloxycarbonyloxyethyl-2-oxo-1-azetidinyl)-2-(1,3-dioxan-5-yl-oxythiocarbonyl)-acetate in 110 ml methylene chloride was cooled to −20° C. under a nitrogen atmosphere. A solution of chlorine in carbon tetrachloride (98 ml of 0.1M solution) was then added. The reaction mixture was stirred at −20° C. for 75 min., then allowed to warm to 0° C. and was washed successively with 75 ml saturated aqueous sodium bicarbonate solution (5° C.), 75 ml H₂O (5° C.) and 75 ml saturated aqueous sodium chloride solution. The organic phase was dried over anhydrous sodium sulfate and concentrated in vacuo yielding 5.97 g of crude title compound. The NMR spectraum in deuterochloroform shows absorptions at 1.5 (d, 3H); 3.4 (m, 1H); 3.8–4.14 (c, 5H); 4.75 (s, 2H); 4.98–5.5 (c, 6H); 5.8–6.2 (c, 1H); 7.5 (m, 4H); 8.2 (m, 4H) ppm.

EXAMPLE 8

Compounds of formula III wherein R is p-nitro benzyloxycarbonyloxyethyl, R₅ is chloro, R₂ is p-nitrobenzyl, X is oxygen and R₁ is as shown in Table IV where prepared according to the procedure of Example 7. For these compounds, NMR spectra were measured in deuterochloroform.

TABLE IV

| R₁ | NMR (ppm) |
|---|---|
| 1-formyl-3-piperidyl (IR(chloroform): 5.6 5.7 and 5.97 microns) | 1.3–2.14 (c,7H); 3.1–4.1 (c,5H); 4.83–5.36 (c,7H); 5.75–6.12 (c,1H); 7.4 (m,4H); 7.94 (b, 1H); 8.1 (m,4H). |
| 1-methoxy-2-propyl | 1.1–1.6 (c,6H); 3.18–3.8 (c,7H); 4.9–5.4 (c,6H); 5.96 (c,1H); 7.48 (m,4H); 8.14 (m,4H) |
| 1,3-dioxolan-2-ylmethyl | 1.5 (m,3H); 3.5–4.0 (c,5H); 4.3 (c,2H); 5.0–5.4 (c,7H); 6.0 (c,1H); 7.5 (m,4H); 8.2 (m,4H) |

TABLE IV-continued

| R₁ | NMR (ppm) |
|---|---|
| 2-pyrrolidinon-3-yl | 1.5 (m,3H); 2.5 (m,2H); 3.3 (m,2H); 3.7 (m,1H); 4.86–5.4 (3,7H); 6.0 (m,1H); 7.48 (c,5H); 8.18 (m,4H). |
| 2-piperidinon-5-yl | 1.5 (m,3H); 1.9–2.94 (C,4H); 3.3–3.94 (c,3H); 4.7–5.5 (c,7H); 5.9 (c,1H); 6.6 (b,1H); 7.5 (m,4H); 8.2 (m,4H) |
| 3-methyl-1,3-oxazolidin-2-on-4-ylmethyl | 1.5 (m,3H); 2.92 (c,3H); 3.3–5.4 (c,12H); 5.9 (c,1H); 7.5 (m,4H); 8.2 (m,4H) |
| 2-methoxyethyl | 1.5 (m,3H); 3.32 (s) and 3.1 3 3.4 (c,4H); 3.62 (m, 2H); 3.96–4.6 (c,3H); 5.1–5.4 (c,5H); 6.0 (c,1H); 7.5 (m,4H); 8.16 (m,4H) |
| 1,3-dioxolan-4-ylmethyl | 1.5 (d,3H); 3.5–4.52 (c, 6H); 4.75–5.42 (c,8H); 6.95 (c,1H); 7.5 (m,4H); 8.2 (m,4H) |

EXAMPLE 9 p-Nitrobenzyl 2-(4-Chloro-2-oxo-1-azetidinyl)-2-(ethoxythiocarbonyl)acetate

To a stirred solution of 214 mg. of p-nitrobenzyl 2-(4-ethylthio-2-oxo-1-azetidinyl)-2-(ethoxythiocarbonyl)acetate in 20 ml of dichloromethane, at ca. 0° C., was added dropwise 8.5 ml. of a 0.1M solution of chlorine in dichloromethane. Stirring was continued for 45 minutes at ca. 0° C. The reaction medium was then diluted with 30 ml. of dichloromethane, and the resulting solution was washed successively with 40 ml. of water, 40 ml. of saturated aqueous sodium bicarbonate and 40 ml. of water. The dried dichloromethane solution was evaporated in vacuo to give the title compounds (387 mg). The IR spectrum (chloroform) of the product showed absorptions at 5.6 and 5.72 microns. The NMR spectrum (deuterochloroform) showed absorptions at 1.4 (m, 3H); 3.0–3.8 (m, 2H); 4.3 (q, 3H); 5.32 and 5.35 (ss, 3H); 5.88 (m, 1H); 7.4 (d, 2H); and 8.2 (d, 2H).

EXAMPLE 10

Chlorination of the appropriate compound of formula VII wherein R is hydrogen, R₁ is as shown in Table V, R₂ is p-nitrobenzyl, R₄ is ethyl, i is zero and X is oxygen, using the procedure of Example 9, afforded the compounds of formula III, R₅ being chloro, in Table V. In Table V, IR spectra were measured as solutions in chloroform, NMR spectra were measured as solutions in deuterochloroform, unless otherwise indicated.

TABLE V

| R₁ | IR (microns) | NMR (ppm) |
|---|---|---|
| 2-methoxyethyl | 5.62 5.72 | 3.0–3.8 (m,7H); 4.18–4.7 (m,2H); 5.2, 5.22 and 5.25 (sss,3H); 5.86 (m,1H); 7.4 (d,2H); 8.05 (d,2H) |
| 2-ethoxyethyl | 5.6 5.7 | 1.25 (m,3H); 3.0–3.94 (m,6H); 4.25–4.86 (m,2H); 5.38 (m,3H); 6.0 (m,1H); 7.6 (d,2H); 8.25 (d,2H) |
| 2-(2-methoxyethoxy)-ethyl | 5.6 5.7 | 3.0–4.0 (m,11H); 4.4 (m,2H); 5.1–5.4 (m,3H); 6.0 (m,1H); 7.6 |

TABLE V-continued

| R₁ | IR (microns) | NMR (ppm) |
|---|---|---|
| 2-phenoxyethyl | 5.6<br>5.7 | 3.0–3.86 (m,2H); 4.22 (m,2H); 4.4–5.0 (m,2H); 5.16, 5.22 and 5.26 (sss,3H); 5.94 (m,1H); 6.64–7.72 (m,7H); 8.1 (m,2H) |
| 2-phenylthioethyl | 5.6<br>5.7 | 3.0–3.95 (m,4H); 4.35 (m,2H); 4.82 (s,1H); 5.3 and 5.35 (s,2H); 5.9 (m,1H); 7.12–7.7 (m,7H); 8.2 (d,2H) |
| 2-azido-ethyl | 4.76<br>5.66 | 3.0–3.8 (m,4H); 4.2–4.8 (m,2H); 5.18–5.5 (m,3H); 5.9 (m,1H); 7.42 (d,2H); 8.17 (d,2H) |
| 2-(acetamido)ethyl | 5.58<br>5.7<br>5.97 (CH₂Cl₂) | 2.02 (s,3H); 2.98–3.98 (m,4H); 4.2–5.82 (m,2H); 5.38 (m,3H); 5.98 (m,1H); 7.1 (m,1H); 7.6 (d,2H); 8.24 (d,2H) |
| 2-(morpholino)ethyl | 5.6<br>5.7 | 2.4–3.94 (m,12H); 4.4 (m,2H); 5.3, 5.34 (s,3H); 6.0 (m,1H); 7.58 (d,2H); 8.2 (d,2H) |
| 2-phenylethyl | 5.6<br>5.72 | 2.9–3.86 (m,4H); 4.45 (m,2H); 5.16–5.4 (m,3H); 5.9 (s,1H); 7.15–7.65 (m,7H); 8.2 (d,2H) |
| 2-(2-thienyl)ethyl | 5.6<br>5.7 | 2.98–3.8 (m,4H); 4.34 (m,2H); 5.18, 5.22 (s,3H); 5.9 (m,1H); 6.7–7.15 (m,3H); 7.4 (d,2H); 8.1 (d,2H) |
| 2-(2-pyridyl)ethyl | 5.6<br>5.7 | 3.0–3.8 (m,4H); 4.6 (m,2H); 5.3 (m,3H); 5.9 (m,1H); 7.3–7.9 (m,5H); 8.16 (d,2H); 8.52 (m,1H) |
| 2-(1-pyrazolyl)ethyl | 5.64<br>5.7 | 3.0–3.6 (m,2H); 4.32–5.06 (m,4H); 5.22 (m,3H); 5.88 (m,1H); 6.2 (m,1H); 7.3–7.64 (m,4H); 8.18 (d,2H) |
| 2-(4-methyl-5-thiazolyl)ethyl | 5.6<br>5.8 | 2.34–3.62 (m,7H); 4.7 (m,2H); 5.3 and 5.35 (ss,3H); 5.96 (m,1H) 7.5 (d,2H); 8.2 (d,2H); 8.7 (s,1H) |
| 2-(2-oxo-1-imidazolidinyl)-ethyl | 5.6<br>5.7<br>1705 | 3.0–3.9 (m,8H); 4.66 (m,2H); 5.4 (m,3H); 6.0 (m,1H); 7.6 (d,2H); 8.22 (d,2H) |
| 2-(2-oxo-1-pyrrolidinyl)-ethyl | 5.58<br>5.67<br>5.94 | 1.7–3.8 (m,10H); 4.64 (m,2H); 5.36 (m,3H); 5.9 (m,1H); 7.58 (d,2H); 8.2 (d,2H) |
| 2-(2-thiazolylthio)-ethyl | 5.6<br>5.7 | 3.0–3.8 (m,4H); 4.56 (m,2H); 5.35 (m,3H); 6.0 (m,1H); 7.46–7.84 (m,4H); 8.3 (d,2H) |
| 2-methoxycyclopentyl- | 5.6<br>5.72 | 1.4–2.0 (m,6H); 3.0–4.0 (m,3H); 3.2 (s,3H); 5.0 (m,1H); 5.4 (s,2H); 6.0 (m,1H); 7.5 (d,2H); 8.2 (d,2H) |
| 2-methoxycyclohexyl | 5.58<br>5.7 | 1.0–1.8 (m,8H); 3.0–3.8 (m,3H); 3.3 (s,3H); 4.8 (m,1H); 5.4 (m,2H); 6.0 (m,1H); 7.6 (d,2H); 8.2 (d,2H) |
| 2-azidocyclohexyl | 4.76<br>5.6<br>5.7 | 1.4–2.2 (m,8H); 3.0–3.8 (m,3H); 5.4 (m,2H); 6.0 (m,1H); 7.6 (d,2H); 8.2 (d,2H) |
| 2-azidocyclopentyl | 4.76<br>5.6<br>5.7 | 1.4–2.0 (m,6H); 3.0–4.0 (m,3H); 5.3 (m,3H); 6.0 (m,1H); 7.6 (d,2H); 8.2 (d,2H) |
| 3-tetrahydrofuranyl | 5.58<br>5.67 | 2.0–2.4 (m,2H); 3.0–3.8 (m,2H); 3.8–4.2 (m,4H); 5.4 (m,3H) 6.0 (m,1H); 7.6 (d,2H); 8.2 (d,2H) |
| 1-acetyl-3-pyrrolidinyl | 5.6<br>5.7 | 1.2–1.4 (m,2H); 2.3 (s,3H); 3.0–4.0 (m,6H); 5.3 (m,3H); 6.0 (m,1H); 7.5 (d,2H); 8.2 (d,2H) |
| 1-acetyl-3-piperidinyl | 5.6<br>5.7 | 1.5–2.2 (m,4H); 2.3 (d,3H); 3.0–4.2 (m,6H); 5.0 (m,1H); 5.4 (s,2H); 6.0 (m,1H); 7.6 (d,2H); 8.2 (d,2H) |
| 2-tetrahydrofuranyl-methyl | 5.6<br>5.8 | 1.8–2.2 (m,4H); 3.0–3.8 (m,5H); 4.2 (s,2H); 5.4 (s,2H); 6.0 (m,1H); 7.5 (d,2H); 8.2 (d,2H) |
| 2-tetrahydropyranyl-methyl | 5.6<br>5.7 | 1.2–2.0 (m,6H); 3.0–4.58 (m,7H); 5.33 (m,3H); 6.0 (m,1H); 7.57 (d,2H); 8.22 (d,2H) |
| 1-acetyl-2-pyrrolidinylmethyl | 5.6<br>5.7 | 1.76–2.58 (m,7H) 3.0–3.84 (m,4H); 3.96–4.7 (m,3H); 5.3 (m,3H); 5.9 (m,1H); 7.58 (d,2H); 8.25 (d,2H) |
| 2-(2-pyridinoylamino)-ethyl | 5.56<br>5.9 | 3.80–4.1 (c,4H); 4.3–4.95 (m,2H); 5.36 (m,3H); 6.0 (m,1H); 7.35–8.8 (c,9H) |
| 1-formyl-3-piperidyl | 5.6<br>5.72 (CH₂Cl₂) | 1.5–2.3 (c,4H); 2.8–4.2 (c,6H); 4.6–6.07 (c,5H); 7.56 (m,2H); 7.82–8.34 (c,3H). |
| N—methylaminocarbonyl-methyl | 5.6<br>5.96 | 2.82 (d,3H); 3.28–3.98 (m,2H); 4.56–5.42 (c,5H); 6.0 (m,1H); 7.6 (c,3H); 8.24 (d,2H). |
| 1-(aminocarbonyl)-ethyl | 5.6<br>5.9 (CH₂Cl₂) | 1.6 (d,3H); 3.1–3.9 (m,2H); 4.83–5.52 (c,4H); 5.82 (m,1H); 6.3 (b,1H); 7.5 (c,3H); 8.2 (d,2H). |
| 2-(methoxymethyl-carbonylamino)ethyl | 5.62<br>5.98 (CH₂CL₂) | 2.92–4.8 (c,11H); 5.35 (m,3H); 6.0 (m,1H); 7.2 (b,1H); 7.6 (d,2H); 8.3 (d,2H). |
| 2-(aminocarbonyloxy)-ethyl | 5.6<br>5.78 | 3.2–5.2 (c,8H); 5.3 (m,3H); 5.9 (m,1H); 7.55 (m,2H); 8.2(d,2H). |
| 1,3-dimethoxy-2-propyl | 5.58 | 2.9–3.84 (c,12H) including 3.34 (s,6H); 5.3 (m,3H); 5.68–6.18 (c,2H); 7.6 (d,2H); 8.26 (d,2H). |
| 2-(2-furylcarbonyl-amino)ethyl | 5.57<br>6.0 (CH₂CL₂) | 3.0–4.04 (c,4H); 4.5 (m,2H); 5.4 (m,3H); 5.98 (m,1H); 6.5 (m,1H); 7.16 (d,1H); 7.6 (c,4H); 8.25 (m,2H). |
| 1,3-dioxan-5-yl | 5.6 | 3.0–4.3 (c,6H); 4.63–5.42 (c,5H); 6.0 (c,1H); 7.5 (m,2H); 8.18 (d,2H). |
| 1-methyl-2-piperidinon-3-yl | 5.62<br>6.02 | 1.7–2.34 (c,4H); 2.84 and 2.94 (s,3H); 3.0–3.64 (c,4H); 4.8–5.5 (c,4H); 5.9 (m,1H); 7.6 (m,2H); 8.2 (m,2H). |
| 1-(aminocarbonylmethyl)-2-piperidinon-3-yl | 5.6<br>6.0 | 1.72–2.4 (c,4H); 3.16–4.44 (c,6H); 4.8–5.5 (c,4H); 5.94 (m,1H); 7.1 (b,2H); 7.52 (m,2H); 8.18 (d,2H); |
| 2-(2-acetylaminoethoxy)- | 5.62 | 2.06 (s,3H); 3.0–4.0 |

TABLE V-continued

| $R_1$ | IR (microns) | NMR (ppm) |
|---|---|---|
| ethyl | 6.0 ($CH_2Cl_2$) | (c,8H); 4.4 (m,2H); 5.3 (m,3H); 6.0 (m,1H); 6.25 (b,1H); 7.54 (d,2H); 8.22 (d,2H); |
| 2-piperidinon-3-yl | 5.6 5.98 ($CH_2Cl_2$) | 1.6–2.4 (c,4H); 2.9–3.9 (c,4H); 4.76–5.4 (c,4H); 5.9 (m,1H); 6.8 (b,1H); 7.54 (d,2H); 8.2 (d,2H). |
| 2-pyrrolidinon-3-yl | 5.6 5.85 ($CH_2Cl_2$) | 2.0–3.9 (c,6H); 4.9–5.5 (c,4H); 5.9 (m,1H); 7.45 (c,3H); 8.1 (d,2H). |
| 2-piperidinon-5-yl | 5.6 6.0 | 1.85–2.6 (c,4H); 3.0–3.8 (c,5H); 5.3 (m,3H); 5.82 (m,1H); 6.6 (b,1H); 7.54 (d,2H); 8.25 (d,2H); |
| 3-methyl-1,3-oxazolid-2-on-4-ylmethyl | 5.6 6.0 | 2.9 (m,3H); 3.15–4.84 (c,7H); 5.34 (m,3H); 5.9 (m,1H); 7.6 (d,2H); 8.25 (d,2H). |
| 1,3-dioxolan-4-ylmethyl | 5.6 ($CH_2Cl_2$) | 3.0–4.4 (c,7H); 4.86 (d,2H); 5.3 (m,3H); 5.9 (m,1H); 7.56 (d,2H); 8.2 (d,2H). |

EXAMPLE 11 p-Nitrobenzyl 6-p-nitrobenzyloxycarbonyloxyethyl-2-(1,3-dioxan-5-yloxy)-2-penem-3-carboxylate, cis and trans isomers A solution of 6.75 g p-nitrobenzyl 2-(4-chloro-3-p-nitrobenzyloxycarbonyloxyethyl-2-oxo-1-azetidinyl)-2-(1,3-dioxan-5-yl-oxythiocarbonyl)-acetate and 17.0 ml diisopropylethylamine in 30 ml methylene chloride was stirred at 25° C. under a nitrogen atmosphere for 3 hours. The reaction mixture was diluted with 150 ml methylene chloride and the resulting solution was washed successively with two 150 ml portion of 1N aqueous hydrochloric acid, 150 ml water and 150 ml saturated aqueous sodium chloride solution. The methylene chloride phase was dried over anhydrous sodium sulfate and concentrated in vacuo. The crude mixture of penems was purified by column chromatography on silica gel. Elution with 15% ethyl acetate in diethyl ether yielded 1.25 g of cis title compound and 480 mg of trans title compound.

The NMR spectrum of the cis title compound in deuterochloroform showed peaks at 1.6 (d, 3H); 3.9–4.34 (c, 6H); 4.84 (s, 2H); 5.0–5.4 (c, 5H); 5.76 (d, 1H); 7.55 (m, 4H); and 8.22 (m, 4H) ppm. The NMR spectrum of the trans title compound in deuterochloroform showed peaks at 1.5 (d, 3H); 3.8–4.38 (c, 6H); 4.84 (s, 2H); 5.0–5.5 (c, 5H); 5.62 (d, 1H); 7.6 (m, 4H); and 8.2 (m, 4H).

EXAMPLE 12

The procedure of Example 11 was employed on the corresponding 4-chloroazetidinyl acetates of formula III to obtain the cis and trans isomers of compounds of formula I listed in Table VI wherein R is p-nitrobenzyloxycarbonyloxyethyl, X is oxygen, $R_1$ is as indicated in Table VI and $R_2$ is p-nitrobenzyl. The NMR spectra were measured in deuterochloroform.

TABLE VI

| $R_1$ | NMR (ppm) |
|---|---|
| 1-formyl-3-piperidyl (trans) (IR(chloroform): 5.64, 5.70, 5.97 microns) | 1.3–2.2 (c,7H); 2.94–4.4 (c,5H); 4.7–5.4 (c,6H); 5.6 (m,1H); 7.5 (m,4H); 7.9 (b,1H); 8.13 (m,4H) |
| (cis) (IR(chloroform): 5.58, 5.71, 5.97 microns) | 1.3–2.2 (c,7H); 3.0–4.46 (c,5H); 4.64–5.45 (c,6H); 5.82 (m,1H); 7.52 (m,4H); 7.96 (b,1H); 8.2 (m,4H) |
| 1,3-dioxolan-4-ylmethyl (trans) | 1.5 (d,3H); 3.6–4.4 (c,6H); 4.95 (d) and 4.7–5.4 (c,7H); 5.6 (d,1H); 7.5 (m,4H); 8.18 (m,4H) |
| (cis) | 1.6 (d,3H); 3.68–4.45 (c,6H); 4.95 (d,2H); 5.05–5.4 (c,5H); 5.74 (d,1H); 7.5 (m,4H); 8.2 (m,4H) |
| 1-methoxy-2-propyl (trans) | 1.2–1.6 (c,6H); 3.35 (s,3H); 3.5 (d,2H); 3.9 (m,1H); 4.2 (b,c,1H); 4.9–5.4 (c,5H); 5.6 (d,1H); 7.54 (m,4H); 8.18 (m,4H) |
| (cis) | 1.14–1.7 (c,6H); 3.36 (s,3H); 3.5 (d,2H); 4.1 (m,1H); 4.3 (b,c,1H); 5.0–5.4 (c,5H); 5.7 (d,1H); 7.54 (m,4H); 8.2 (m,4H) |
| 1,3-dioxolan-2-ylmethyl (trans) | 1.5 (d,3H); 3.8–4.12 (c,5H); 4.2 (a,2H); 5.0–5.44 (c,6H); 5.62 (d,1H); 7.56 (m,4H); 8.2 (m,4H) |
| (cis) | 1.6 (d,3H); 3.8–4.12 (c,5H); 4.2 (d,2H); 5.0–5.5 (c,6H); 5.75 (d,1H); 7.52 (m,4H); 8.2 (m,4H) |
| 2-pyrrolidinon-3-yl (trans) | 1.5 (d,3H); 2.5 (m,2H); 3.36 (m,2H); 3.92 (m,1H); 4.7 (m,1H); 4.9–5.4 (c,5H); 5.54–5.65 (d,1H); 7.1 (b,1H); 7.52 (m,4H); 8.18 (m,4H) |
| (cis) | 1.6 (d,3H); 2.44 (m,2H); 3.34 (m,2H); 4.06 (m,1H); 4.72 (m,1H); 4.9–5.4 (c,5H); 7.5 (m,4H); 8.18 (m,4H) |
| 2-piperidinon-5-yl (trans) | 1.5 (d,3H); 1.86–2.68 (c,4H); 3.56 (c,2H); 3.86 (m,1H); 4.56 (c,1H); 5.0–5.32 (c,5H); 5.6 (d,1H); 6.6 (b,1H); 7.48 (m,4H); 8.2 (m,4H) |
| (cis) | 1.6 (d,3H); 1.9–2.68 (c,4H); 3.6 (c,2H); 4.1 (m,1H); 4.62 (c,1H); 4.9–5.46 (c,5H); 5.76 (d,1H); 7.0 (b,1H); 7.5 (m,4H); 8.2 (m,4H) |
| 3-methyl-1,3-oxazolid-2-on-4-ylmethyl (trans) | 1.48 (d,3H); 2.9 (s,3H); 3.76–4.46 (c,6H); 4.95–5.36 (c,5H); 5.62 (d,1H); 7.52 (m,4H); 8.2 (m,4H) |
| (cis) | 1.58 (d,3H); 2.9 (s,3H); 3.8–4.44 (c,6H); 4.94–5.30 (c,5H); 5.74 (d,1H); 7.5 (m,4H); 8.18 (m,4H) |
| 2-methoxyethyl (trans) | 1.48 (d,3H); 3.36 (s,3H); 3.62 (m,2H); 3.86 (m,1H); 4.3 (m,2H); 5.0–5.36 (c,5H); 5.56 (d,1H); 7.46 (m,4H); 8.16 (m,4H) |
| (cis) | 1.6 (d,3H); 3.36 (s,3H); 3.64 (m,2H); 3.9–4.4 (c,3H); 5.1–5.36 (c,5H); 5.7 (d,1H); 7.5 (m,4H); 8.18 (m,4H) |

EXAMPLE 13 p-Nitrobenzyl 6-p-nitrobenzyloxycarbonyloxyethyl-2-(1,3-dioxan-5-yloxy)-2-penem-3-carboxylate, trans isomer A solution of 960 mg p-nitrobenzyl 6-p-nitrobenzyloxycarbonyloxyethyl-2-(1,3-dioxan-5-yloxy)-2-penem-3-carboxylate, cis isomer, 96 mg hydroquinone and 150 ml toluene was refluxed under a nitrogen atmosphere for 90 min. The reaction mixture was cooled to 25° C. and concentrated in vacuo. The residue was dissolved in 100 ml ethyl acetate and the resulting solution was washed successively with two 100 ml portions 1N aqueous sodium hydroxide solution, 100 ml water and 100 ml saturated aqueous sodium chloride solution. The ethyl acetate solution was dried over anhydrous sodium sulfate and concentrated in vacuo. The residue was chromatographed on silica gel. Elution with 15% ethyl acetate-diethyl ether yielded 425 mg of the starting cis penem and 300 mg of the title compound.

EXAMPLE 14 p-Nitrobenzyl 2-Ethoxy-2-penem-3-carboxylate

To a solution of 387 mg. of p-nitrobenzyl 2-(4-chloro-2-oxo-1-azetidinyl)-2-(ethoxythiocarbonyl)acetate in 20 ml. of dichloromethane was added 1.74 ml. of diisopropylethylamine. The reaction mixture was stirred overnight at room temperature and then it was diluted with 30 ml. of dichloromethane. The resulting solution was washed successively with 40 ml. of dilute hydrochloric acid (2 times) and 40 ml. of water (2 times), and then it was dried using anhydrous sodium sulfate. Evaporation in vacuo gave the title compound as a yellow viscous liquid. This crude product was purified by column chromatography on 35 g. of silica gel, eluting with 95:5 chloroform-ethyl acetate. The fractions containing the product were combined and evaporated in vacuo to give the title compound as a solid (yield: 100 mg). The IR spectrum in chloroform of the product showed absorptions at 5.6 and 5.88 microns. The NMR spectrum in deuterochloroform showed absorptions at 1.45 (t, 3H); 3.21–4.1 (m, 2H); 4.25 (q, 2H); 5.25 (d, 2H); 5.6 (m, 1H); 7.5 (d, 2H); and 8.1 (d, 2H) ppm.

EXAMPLE 15

Cyclization of the appropriate compound of formula III wherein R is hydrogen, $R_1$ is as shown in Table VII, $R_2$ is p-nitrobenzyl, $R_5$ is chloro and X is oxygen with diisopropylethylamine, substantially according to the procedure of Example 14, afforded the corresponding compounds of formula I in Table VII. For the compounds in Table VII, NMR spectra were measured in deuterochloroform unless otherwise indicated, IR spectra were measured in the medium indicated.

TABLE VII

| $R_1$ | IR microns | NMR (ppm) |
|---|---|---|
| 2-methoxyethyl | 5.57<br>5.88<br>(CHCl₃) | 3.25–4.0 (m,7H); 4.3 (t,2H); 5.3 (d,2H); 5.65 (m,1H); 7.54 (d,2H); 8.2 (d,2H) |
| 2-ethoxyethyl | 5.58<br>5.88<br>(CHCl₃) | 1.16 (t,3H); 3.2–4.08 (m,6H); 4.32 (m,2H); 5.3 (d,2H); 5.62 (M,1H); 7.58 (d,2H); 8.2 (d,2H) |
| 2-(2-(methoxy)-ethoxy)ethyl | 5.6<br>5.7<br>5.88 | 3.22–4.1 (m,11H); 4.36 (m,2H); 5.32 (d,2H); 5.68 (m,1H); 7.6 (d,2H); 8.2 (d,2H) |
| 2-phenoxyethyl | 5.57<br>5.88<br>(CHCl₃) | 3.2–4.0 (m,2H); 4.25 (m,2H); 4.55 (m,2H); 5.3 (d,2H); 5.7 (m,1H); 6.75–7.42 (m,5H); 7.5 (d,2H); 8.1 (d,2H) |
| 2-(phenylthio)ethyl | 5.57<br>5.88<br>(CH₂Cl₂) | 3.2–4.0 (m,6H); 5.3 (d,2H); 5.65 (m,1H); 7.1–7.7 (m,7H); 8.2 (d,2H) |
| 2-(azido)ethyl | 4.76<br>5.56<br>5.88<br>(CHCl₃) | 3.25–4.06 (m,4H); 4.3 (t,2H); 5.3 (d,2H); 5.68 (m,1H); 7.55 (d,2H); 8.2 (d,2H) |
| 2-(acetamido)ethyl | 5.58<br>5.88<br>6.0<br>(CHCl₃) | 1.95 (s,3H); 3.22–4.4 (m,6H); 5.3 (d,2H); 5.65 (m,1H); 6.6 (m,1H); 7.6 (d,2H); 8.26 (d,2H) |
| 2-morpholino)ethyl | 5.58<br>5.88<br>(CHCl₃) | 2.3–3.0 (m,6H); 3.16–4.1 (m,6H); 4.34 (t,2H); 5.3 (d,2H); 5.66 (m,1H); 7.6 (d,2H); 7.8 (d,2H) |
| 2-phenylethyl | 5.58<br>5.88<br>(CH₂Cl₂) | 3.15–4.05 (m,4H); 4.45 (t,2H); 5.36 (d,2H); 5.68 (m,1H); 7.14–7.62 (m,7H); 8.25 (d,2H) |
| 2-(2-thienyl)ethyl | 5.58<br>5.86<br>(CHCl₃) | 3.0–4.1 (m,4H); 4.36 (t,3H); 5.3 (d,2H); 5.6 (m,1H); 6.74–7.3 (m,3H); 7.5 (d,2H); 8.14 (d,2H) |
| 2-(2-pyridyl)ethyl | 5.58<br>5.88<br>(CHCl₃) | 3.1–4.06 (m,4H); 4.66 (t,2H); 5.3 (d,2H); 5.68 (m,1H); 7.04–7.82 (m,5H); 8.26 (d,2H); 8.62 (m,1H) |
| 2-(1-pyrazolyl)ethyl | 5.58<br>5.88<br>(CH₂Cl₂) | 3.2–4.04 (m,2H); 4.54 (m,4H); 5.32 (d,2H); 5.62 (m,1H); 6.25 (m,1H); 7.2–7.7 (m,4H); 8.2 (d,2H) |
| 2-(4-methyl-5-thiazolyl)ethyl | 5.57<br>5.87<br>(CH₂Cl₂) | 2.42 (s,3H); 3.06–4.08 (m,3H); 4.38 (t,2H); 5.32 (d,2H); 5.65 (m,1H); 7.6 (d,2H); 8.2 (d,2H); 8.6 (s,1H) |
| 2-(2-oxo-1-imidazolidinyl)ethyl | 5.58<br>5.88<br>(CHCl₃) | 3.04–3.8 (m,8H); 4.28 (m,2H); 5.24 (d,2H); 5.6 (m,1H); 7.5 (d,2H); 8.1 (d,2H) |
| 2-(2-oxo-1-pyrrolidinyl)ethyl | 5.58<br>5.98<br>(CHCl₃) | 1.7–2.6 (m,4H); 3.3–4.5 (m,8H); 5.34 (d,2H); 5.7 (m,1H); 7.62 (d,2H); 8.26 (d,2H) |
| 2-(2-thiazolylthio)ethyl | 5.58<br>5.88<br>(CHCl₃) | 3.35–4.1 (m,4H); 4.5 (t,2H); 5.26 (s,2H); 5.72 (m,1H); 7.46–7.8 (m,4H); 8.2 (d,2H) (DMSO-d₆) |
| 2-methoxycyclopentyl | 5.58<br>5.88<br>(CHCl₃) | 1.4–2.0 (m,6H); 3.3 (s,3H); 2.8–4.0 (m,2H); 3.7–4.1 (m,1H); 4.5 (m,1H); 5.3 (s,2H); 5.7 (m,1H); 7.6 (d,2H); 8.2 (d,2H) |
| 2-methoxycyclohexyl | 5.60<br>5.85<br>(CHCl₃) | 1.2–2.0 (m,8H); 2.8–4.0 (m,2H); 3.4 (s,3H); 3.8–4.2 (m,2H); 5.3 (d,2H); 5.6 (s,1H); 7.6 (d,2H); 8.2 (d,2H) |
| 2-azidocyclohexyl | 4.76<br>5.65<br>5.85<br>(CHCl₃) | 1.2–2.0 (m,8H); 3.0–4.0 (m,4H); 5.3 (d,2H); 5.7 (q,1H); 7.6 (d,2H); 8.2 (d,2H) |
| 2-azidocyclopentyl | 4.75<br>5.65<br>5.85<br>(CHCl₃) | 1.4–2.0 (m,6H); 2.9–4.0 (m,3H); 4.3 (m,1H); 5.2 (d,2H); 5.6 (q,1H); 7.5 (d,2H); 8.2 (d,2H) |
| 2-tetrahydrofuranyl | 5.58<br>5.85<br>(CHCl₃) | 2.0–2.4 (m,2H); 2.9–4.0 (m,2H); 3.4–4.1 (m,4H); 4.9 (m,1H); 5.3 (d,2H); 5.7 (q,1H); 7.6 |

TABLE VII-continued

| R$_1$ | IR microns | NMR (ppm) |
|---|---|---|
| | | (d,2H); 8.3 (d,2H) |
| 1-acetyl-3-pyrrolidinyl | 5.58 5.85 (CHCl$_3$) | 1.2–1.6 (m,2H); 2.0 (s,3H); 3.4–4.0 (m,4H); 5.0 (m,1H); 5.4 (d,2H); 5.7 (m,1H); 7.6 (d,2H); 8.2 (d,2H) |
| 1-acetyl-3-piperidinyl | 5.58 5.85 (CHCl$_3$) | 1.2–2.0 (m,4H); 2.0 (s,3H); 3.0–4.4 (m,7H); 5.3 (s,2H); 5.7 (s,1H); 7.6 (d,2H); 8.2 (d,2H) |
| 2-tetrahydrofuranylmethyl | 5.60 5.86 (CHCl$_3$) | 1.8–2.1 (m,4H); 2.9–4.0 (m,2H); 3.8–4.1 (m,3H); 4.2 (s,2H); 5.3 (d,2H); 5.6 (q,1H); 7.6 (d,2H); 8.2 (d,2H) |
| 2-tetrahydropyranylmethyl | 5.58 5.88 (CHCl$_3$) | 1.14–1.96 (m,6H); 3.16–4.28 (m,7H); 5.3 (d,2H); 5.68 (m,1H); 7.6 (d,2H); 8.2 (d,2H) |
| 1-acetyl-2-pyrrolidinylmethyl | 5.58 5.88 (CHCl$_3$) | 1.7–2.3 (m,7H); 3.22–4.02 (m,4H); 4.02–4.52 (m,3H); 5.34 (d,2H); 5.68 (m,1H); 7.6 (d,2H); 8.22 (d,2H) |
| 2-(2-pyridinoyl-amino)ethyl | 5.57 5.85 6.0 (CH$_2$Cl$_2$) | 3.23–4.6 (c,6H); 5.4 (d,2H); 5.62 (m,1H); 7.25–8.7 (c,9H) |
| 1-formyl-3-piperidyl (less polar diastereomer) | | 1.08–2.3 (c,4H); 3.04–4.44 (c,7H); 5.3 (d,2H); 5.6 (m,1H); 7.54 (d,2H); 7.93 (d,1H); 8.14 (d,2H) |
| (more polar diastereomer) | | 1.1–2.66 (c,4H); 3.1–4.47 (c,7H); 5.3 (s,2H); 5.7 (m,1H); 7.58 (d,2H); 7.96 (s,1H); 8.2 (d,2H) |
| N—methylaminocarbonylmethyl | 5.56 5.84 5.92 5.97 (CHCl$_3$) | 2.8 (d,3H); 3.3–3.84 (m,2H); 4.6 (s,2H); 5.32 (d,2H); 5.7 (m,1H); 7.62 (c,3H); 8.2 (d,2H) |
| 1-(aminocarbonyl)-ethyl | 5.56 5.85 5.95 (CHCl$_3$) | 1.46 (d,3H); 3.12–4.08 (m,2H); 4.68 (q,1H); 5.34 (d,2H); 5.72 (m,1H); 7.5 (b,2H); 7.7 (d,2H); 8.26 (d,2H) (DMSO-d$_6$) |
| 2-(methoxymethyl carbonylamino) ethyl | 5.58 5.96 (CH$_2$Cl$_2$) | 3.45 (s,3H); 3.5–4.1 (c) and 3.95 (s,2H) (total 6H); 4.35 (t,2H); 5.4 (d,2H); 5.7 (c,1H); 7.15 (b,1H); 7.64 (d,2H); 8.26 (d,2H) |
| 2-(aminocarbonyloxy) ethyl | 5.58 5.78 5.88 (CHCl$_3$) | 3.2–4.5 (e,6H); 5.25 (m,2H); 5.64 (m,1H); 6.25 (b,2H); 7.5 (d,2H); 8.1 (d,2H) |
| 1,3-dimethoxy-2-propyl | 5.57 5.84 (CHCl$_3$) | 3.34 (s,6H); 3.3–4.2 (c,6H); 4.4 (m,1H); 5.26 (d,2H); 5.6 (m,1H); 7.54 (d,2H); 8.14 (d,2H) |
| 2-(2-furylcarbonyl-amino)ethyl | 5.56 5.84 6.0 (CHCl$_3$) | 3.2–4.5 (c,6H); 5.3 (d,2H); 5.6 (m,1H); 6.42 (m,1H); 7.0 (m,1H); 7.05 (d,1H); 7.36 (m,1H); 7.54 (d,2H); 8.15 (d,2H) |
| 1,3-dioxan-5-yl | 5.57 5.88 (CHCl$_3$) | 3.23–4.37 (c,7H); 4.8 (s,2H); 5.29 (d,2H); 5.64 (m,1H); 7.57 (d,2H); 8.14 (d,2H) |
| 1-methyl-2-piperidinon-3-yl | 5.57 5.88 6.0 (CHCl$_3$) | 1.7–2.4 (c,4H); 2.94 (s,3H); 3.18–3.8 (c,4H); 4.56 (m,1H); 5.3 (d,2H); 5.65 (m,1H); 7.6 (d,2H); 8.2 (d,2H) |
| 1-(aminocarbonyl-methyl)-2-piperidinon-3-yl | 5.57 5.88 6.0 (CHCl$_3$) | 1.7–2.4 (c,4H); 3.1–4.1 (c,6H); 4.6 (m,1H); 5.26 (m,2H); 5.6 (m,1H); 6.1 (b,1H); 6.5 (b,1H); 7.5 (d,2H); 8.2 (d,2H) |
| 2-(2-acetylamino-ethoxy)ethyl | 5.56 5.88 | 1.9 (s,3H); 3.1–4.1 (c,8H); 4.3 (m,2H); 5.62 |
| | 6.0 (CHCl$_3$) | (m,1H); 7.1 (b,1H); 5.24 (m,2H); 7.54 (d,2H); 8.12 (d,2H) |
| 2-piperidinon-3-yl | 5.57 5.88 5.98 (CHCl$_3$) | 1.6–2.4 (c,4H); 3.0–4.1 (c,4H); 4.54 (m,1H); 5.28 (m,2H); 5.7 (m,1H); 7.6 (d,2H); 7.85 (b,1H); 8.2 (d,2H) |
| 2-pyrrolidinon-3-yl | 5.55 5.85 5.9 (CHCl$_3$) | 2.02 (m,2H); 3.06–4.06 (c,4H); 4.86 (m,1H); 5.3 (d,2H); 5.74 (m,1H); 7.5 (b,1H); 7.64 (d,2H); 8.22 (d,2H) (DMSO-d$_6$) |
| 2-piperidinon-5-yl | 5.57 5.85 6.0 (CHCl$_3$) | 1.9–2.3 (c,4H); 3.22–4.14 (c,5H); 5.25 (s,2H); 5.74 (m,1H); 7.4 (b,1H); 7.6 (d,2H); 8.2 (d,2H) |
| 3-methyl-1,3-oxazolid-2-on-4-ylmethyl | 5.57 5.7 5.88 (CHCl$_3$) | 2.9 (s,3H); 3.24–4.5 (c,7H); 5.2 (d,2H); 5.6 (m,1H); 7.45 (d,2H); 8.1 (d,2H) |
| 1,3-dioxolan-4-ylmethyl | 5.57 5.88 (CHCl$_3$) | 3.2–4.5 (c,7H); 4.9 (d,2H); 5.26 (d,2H); 5.64 (m,1H); 7.58 (d,2H); 8.2 (d,2H). |

EXAMPLE 16

2-Ethoxy-2-penem-3-carboxylic Acid, Calcium Salt

A suspension of 140 mg. of 5% palladium on calcium carbonate in 10 ml. of water was shaken under an atmosphere of hydrogen at a pressure of ca 55 psi. until hydrogen uptake ceased. A solution of 140 mg. of p-nitrobenzyl 2-ethoxy-2-penem-3-carboxylate in 10 ml. of tetrahydrofuran was added, and this mixture was shaken under an atmosphere of hydrogen at a pressure of ca 55 psi. for 1 hour. The catalyst was then removed by filtration and the tetrahydrofuran was removed from the filtrate by evaporation in vacuo. The resulting aqueous solution was washed with ethyl acetate, and then it was lyophilized to give the title compound as an amorphous solid 50 mg. The IR spectrum (potassium bromide disc) showed an absorption at 5.7 microns. The NMR spectrum (deuterochloroform) showed peaks at 1.4 (t, 3H); 3.2–4.4 (m, 4H); and 5.58 (m, 1H) ppm.

EXAMPLE 17

Hydrogenolysis of compounds of formula I wherein R is hydrogen, R$_1$ is as indicated in Table VII, R$_2$ is p-nitrobenzyl and X is oxygen, according to the procedure of Example 13, afforded the compounds of formula I wherein R$_2$ is the calcium ion, shown in Table VIII. The IR and NMR spectra were measured in the media indicated.

TABLE VIII

| R$_1$ | IR (microns) | NMR (ppm) |
|---|---|---|
| 2-methoxyethyl | 5.7 (KBr disc) | 3.25 (s,3H); 3.2–4.1 (m,4H); 4.2 (m,2H); 5.5 (m,1H) (DMSO-d$_6$) |
| 2-ethoxyethyl | 5.65 (KBr disc) | 1.1 (t,3H); 3.2–3.88 (m,6H); 4.22 (m,2H); 5.56 (m,1H) (DMSO-d$_6$) |
| 2-(2-methoxy-ethoxy)ethyl | 5.65 (CHCl$_3$) | 3.16–3.86 (m,11H); 4.22 (m,2H); 5.56 (m,1H) (DMSO-d$_6$) |
| 2-phenoxyethyl | 5.75 (KBr disc) | 3.2–4.0 (m,2H); 4.2 (m,2H); 4.42 (m,2H); 5.54 (m,1H); 6.76 (m,5H) (DMSO-d$_6$) |

TABLE VIII-continued

| $R_1$ | IR (microns) | NMR (ppm) |
|---|---|---|
| 2-(phenylthio)ethyl | 5.7 (KBr disc) | 3.14–3.9 (m,4H); 4.22 (m,2H); 5.52 (m,1H); 7.04–7.56 (m,5H) (DMSO-$d_6$) |
| 2-azidoethyl | 4.75 5.7 (KBr disc) | 3.3–3.98 (m,4H); 4.3 (m,2H); 5.66 (m,1H) (DMSO-$d_6$) |
| 2-(acetamido)ethyl | 5.65 6.10 (KBr disc) | 1.82 (s,3H); 3.18–4.1 (m,6H); 5.56 (m,1H); 9.0 (m,1H) (DMSO-$d_6$) |
| 2-(morpholino)ethyl | 5.65 (CHCl$_3$) | 2.32–2.7 (m,6H); 3.26–3.98 (m,6H); 4.22 (m,2H); 5.62 (m,1H) (DMSO-$d_6$) |
| 2-phenylethyl | 5.75 (KBr disc) | 2.98 (m,2H); 3.3–4.0 (m,2H); 4.3 (m,2H); 5.58 (m,1H); 7.3 (s,5H) (DMSO-$d_6$) |
| 2-(2-thienyl)ethyl | 5.75 (KBr disc) | 3.1–3.88 (m,4H); 4.3 (m,2H); 5.54 (m,1H); 6.94 (m,2H); 7.34 (m,1H) (DMSO-$d_6$) |
| 2-(2-pyridyl)ethyl | 5.75 (KBr disc) | 3.02–3.92 (m,2H); 4.46 (m,2H); 5.54 (m,1H); 7.14–7.44 (m,2H); 7.7 (m,1H); 8.5 (m,1H); (DMSO-$d_6$) |
| 2-(1-pyrazolyl)ethyl | 5.65 (KBr disc) | 3.1–3.9 (m,2H); 4.46 (m,4H); 5.54 (m,1H); 6.23 (m,1H); 7.48 (m,1H); 7.8 (m,1H) (DMSO-$d_6$) |
| 2-(4-methyl-5-thiazolyl)ethyl | 5.65 (KBr disc) | 2.36 (s,3H); 2.96–4.0 (m,4H); 4.3 (m,2H); 5.56 (m,1H); 8.8 (s,1H) (DMSO-$d_6$) |
| 2-(2-oxo-1-imidazolidinyl)ethyl | 5.75 (KBr disc) | 2.96–3.8 (m,8H); 4.14 (m,2H); 5.58 (m,1H) (DMSO-$d_6$) |
| 2-(2-oxo-1-pyrrolidinyl) | 5.65 (KBr disc) | 1.6–2.46 (m,4H); 3.0–4.44 (m,8H); 5.56 (m,1H) (DMSO-$d_6$) |
| 2-(2-thiazolylthio)ethyl | 5.65 (KBr disc) | 3.22–3.96 (m,4H); 4.4 (m,2H); 5.58 (m,1H); 7.72 (m,2H) (DMSO-$d_6$) |
| 2-methoxycyclopentyl | 5.65 6.25 (DMSO) | |
| 2-methoxycyclohexyl | 5.65 6.25 (DMSO) | |
| 2-azidocyclohexyl | 4.75 5.65 6.25 (DMSO) | |
| 2-aminocyclopentyl | 5.65 6.25 (DMSO) | |
| 2-tetrahydrofuranyl | 5.65 6.25 (DMSO) | |
| 1-acetyl-3-pyrrolidinyl | 5.7 6.20 (KBr disc) | |
| 1-acetyl-3-piperidinyl | 5.65 6.10 6.15 (DMSO) | |
| 2-tetrahydrofuranylmethyl | 5.65 6.25 (DMSO) | |
| 2-tetrahydropyranylmethyl | 5.65 (KBr disc) | 0.98–1.88 (m,6H); 3.04–4.22 (m,7H); 5.56 (m,1H) (DMSO-$d_6$) |
| 1-acetyl-2-pyrrolidinylmethyl | 5.62 (KBr disc) | 1.7–2.14 (m,7H); 3.08 (m,7H); 5.54 (m,1H) (DMSO-$d_6$) |
| 2-(2-pyridinoyl-amino)ethyl | 5.65 6.0 (KBr disc) | 3.15–3.9 (c,4H); 4.25 (m,2H); 5.55 (m,1H); 7.6 (m,1H); 8.05 (m,2H); 8.65 (m,1H); 9.05 (m,1H) (DMSO-$d_6$) |
| 1-formyl-3-piperidyl | 5.68 5.93 (DMSO) | |
| N—methylaminocarbonylmethyl | 5.65 6.0 (Kbr disc) | 2.62 (d,3H); 3.2–3.94 (m,2H); 4.44 (s,2H); 5.64 (m,1H) (DMSO-$d_6$) |
| 1-(aminocarbonyl)ethyl | 5.65 5.9 6.25 (KBr disc) | 1.42 (d,3H); 3.1–4.0 (m,2H); 4.6 (m,1H); 5.7 (m,1H) (DMSO$d$-$_6$) |
| 2-(methoxymethylcarbonylamino)ethyl | 5.65 6.05 (KBr disc) | 3.1–4.3 (c) and 3.3 (s,3H) (total 11H); 5.58 (m,1H); 8.46 (b,1H) (DMSO-$d_6$) |
| 2-(aminocarbonyloxy)ethyl | 5.75 5.85 (KBr disc) | 3.2–4.7 (c,6H); 5.56 (m,1H); 6.6 (b,2H) (DMSO-$d_6$) |
| 1,3-dimethoxy-2-propyl | 5.7 (KBr disc) | 3.4 (s,6H); 3.3–3.94 (c,6H); 4.48 (m,1H); 5.66 (m,1H) (DMSO-$d_6$ and $D_2O$) |
| 2-(2-furylcarbonylamino)ethyl | 5.65 6.2 (KBr disc) | 3.2–3.9 (c,4H); 4.2 (m,2H); 5.58 (m,1H); 6.6 (m,1H); 7.32 (m,1H); 7.82 (m,1H); 9.18 (m,1H) (DMSO-$d_6$) |
| 1,3-dioxan-5-yl | 5.65 (KBr disc) | 3.2–4.4 (c,7H); 4.82 (s,2H); 5.56 (m,1H) (DMSO-$d_6$) |
| 1-methyl-2-piperidinon-3-yl | 5.6 6.1 (KBr disc) | 1.64–2.28 (c,4H); 2.84 (s,3H); 3.14–3.9 (c,4H); 4.66 (m,1H); 5.58 (m,1H) (DMSO-$d_6$) |
| 1-(aminocarbonylmethyl)-2-piperidinon-3-yl | 5.7 6.0 6.1 (KBr disc) | 1.7–2.36 (c,4H); 3.14–4.06 (c,6H); 4.74 (m,1H); 5.56 (m,1H); 7.14 (b,1H); 7.56 (b,1H) (DMSO-$d_6$) |
| 2-(2-acetylaminoethoxy)ethyl | 5.7 6.0 (KBr disc) | 1.82 (s,3H); 3.06–4.42 (c,10H); 5.58 (m,1H); 8.08 (b,1H) (DMSO-$d_6$) |
| 2-piperidino-3-yl | 5.7 6.1 (KBr disc) | 1.5–2.3 (c,4H); 2.94–4.0 (c,4H); 4.6 (m,1H); 5.56 (m,1H); 8.16 (b,1H) (DMSO-$d_6$) |
| 2-pyrrolidinon-3-yl | 5.65 5.90 (KBr disc) | |
| 2-piperidinon-5-yl | 5.7 6.1 (KBr disc) | 1.78–2.46 (c,4H); 3.1–4.2 (c,5H); 5.6 (m,1H); 7.56 (b,1H) (DMSO-$d_6$) |
| 3-methyl-1,3-oxazolid-2-on-4-ylmethyl | 5.65 (KBr disc) | 2.8 (m,3H); 3.2–4.54 (c,7H); 5.6 (m,1H) (DMSO-$d_6$) |
| 1,3-dioxolan-4-ylmethyl | 5.7 (KBr disc) | 3.2–4.4 (c,7H); 4.86 (d,2H); 5.56 (m,1H) (DMSO-$d_6$) |

EXAMPLE 18

Trans-6-hydroxyethyl-2-(1,3-dioxan-5-yloxy)-2-penem-3-carboxylic acid, calcium salt The procedure of Example 16 was employed for the hydrogenolysis of p-nitrophenyl trans-6-p-nitrobenzyloxycarbonyloxyethyl-2-(1,3-dioxan-5-yloxy)-2-penem-3-carboxylate to obtain 205 mg of the title compound. The infrared spectrum of the title compound in a potassium bromide disc showed absorptions at 2.93 and 5.65 microns.

EXAMPLE 19

The procedure of Example 16 was employed for the corresponding compounds listed in Table VI to obtain compounds of formula I wherein R is hydroxyethyl, X is oxygen, $R_2$ is a calcium dication and $R_1$ is as indicated in Table IX along with the IR spectra measured as a potassium bromide disc.

TABLE IX

| R₁ | IR (microns) |
| --- | --- |
| 1-formyl-3-piperidyl (trans) | 2.92, 5.64, 6.0 |
| 1,3-dioxolan-4-ylmethyl (trans) | 2.94, 5.65 |
| 1-methoxy-2-propyl (trans) | 2.92, 5.7 |
| 1,3-dioxolan-2-ylmethyl (trans) | 2.92, 5.7 |
| 2-pyrrolidinon-3-yl (trans) | 2.9, 5.7, 5.9 |
| 2-piperidinon-5-yl (trans) | 2.94, 5.7, 6.0 |
| 3-methyl-1,3-oxazolidin-2-on-4-yl-methyl (trans) | 2.92, 5.56, 5.72 |
| 2-methoxyethyl (trans) | 2.9, 5.7 |

PREPARATION A p-Nitrobenzyl 2-(4-Ethylthio-2-oxo-1-azetidinyl)-2-(ethoxythiocarbonylthio)acetate To a stirred mixture of 3.2 g. of potassium ethyl xanthate, 5.4 g. of benzyltriethylammonium chloride, 100 ml. of water and 50 ml. of dichloromethane, at 0° C., was added a solution of 7.12 g. of p-nitrobenzyl 2-(4-ethylthio-2-oxo-1-azetidinyl)-2-chloroacetate in 75 ml. of dichloromethane. Stirring was continued at 0°–5° C. for 1 hour, and then the organic phase was removed. The aqueous phase was extracted with 100 ml. of dichloromethane, and then the combined dichloromethane layers were washed successively with 75 ml. of dilute hydrochloric acid, 75 ml. of saturated aqueous sodium bicarbonate and 75 ml. of water. The dichloromethane solution was dried with anhydrous sodium sulfate and evaporated to dryness in vacuo, and the residue was purified by column chromatography on 200 g. of silica gel, eluting with 95:5 chloroform-ethyl acetate. The product containing fractions were combined and concentrated in vacuo to give 4.3 g of the title compound. The IR spectrum (chloroform) showed an absorption at 5.66 microns. The NMR spectrum (deuterochloroform) showed peaks at 1.02–1.6 (m, 6H); 2.35–3.65 (m, 4H); 4.4–5.1 (m, 3H); 5.3 (s, 2H); 6.3 and 6.4 (ss, 1H); 7.4 (d, 2H); and 8.2 (d, 2H) ppm.

PREPARATION B

Reaction of p-nitrobenzyl 2-(4-ethythio-2-oxo-1-azetidinyl)-2-chloroacetate with the appropriate xanthate salt of the formula $K^+R_1-O-(C=S)-S^-$, whose $R_1$ is shown in Table X, according to the procedure of Preparation A, afforded the corresponding compounds formula VI in Table X. The IR spectra were measured for chloroform solutions and the NMR spectra were measured for deuterochloroform solutions.

TABLE X

| R₁ | IR (microns) | NMR (ppm) |
| --- | --- | --- |
| 2-methoxyethyl | 5.66 | 1.23 (t,3H); 2.4–3.84 (m,9H); 4.56–5.14 (m,3H); 5.3 (s,2H); 6.24 and 6.3 (ss,1H); 7.42 (d,2H); 8.16 (d,2H) |
| 2-ethoxyethyl | 5.65 | 1.0–1.4 (m,6H) 2.4–3.9 (m,8H); 4.6–5.18 (m,3H); 5.34 (s,2H); 6.3 and 6.36 (ss,1H); 7.52 (d,2H); 8.22 (d,2H) |
| 2-(2-(methoxyethoxy)ethyl | 6.63 | 1.22 (t,3H); 2.4–4.0 (m,13H); 4.62–5.2 (m,3H); 5.33 (s,2H); 6.34 and 6.4 (ss,1H); 7.58 (d,2H); 8.25 (d,2H) |
| 2-phenoxyethyl | 5.66 | 1.2 (m,3H); 2.3–3.55 (m,4H); 4.2 (m,2H); 4.6–5.1 (m,3H); 5.22 (s,2H); 6.2 and 6.3 (ss,1H); 6.68–7.56 (m,7H); 8.12 (d,2H) |
| 2-(phenylthio)ethyl | 5.66 5.7 | 1.22 (t,3H); 2.38–3.9 (m,6H); 4.6–5.14 (m,3H); 5.3 (s,2H); 6.3 and 6.42 (ss,1H); 7.2–7.68 (m,7H); 8.2 (d,2H) |
| 2-azidoethyl | 4.76 5.6 | 1.22 (t,3H); 2.38–3.82 (m,6H); 4.6–5.14 (m,3H); 5.3 (s,2H); 6.3 and 6.4 (ss,1H); 7.5 (d,2H); 8.2 (d,2H) |
| 2-(acetamido)ethyl | 5.66 6.0 | 1.3 (t,3H); 2.08 (s,3H); 2.46–3.9 (m,6H); 4.5–5.35 (m,3H); 5.42 (s,2H); 6.43 and 6.56 (ss,1H); 6.9 (m,1H); 7.6 (d,2H); 8.32 (d,2H) |
| 2-(morpholino)ethyl | 5.66 | 1.25 (t,3H); 2.4–3.86 (m,14H); 4.6–5.26 (m,3H); 5.36 (s,2H); 6.36 and 6.42 (ss,1H); 7.57 (d,2H); 8.22 (d,2H) |
| 2-phenylethyl | 5.66 | 1.25 (t,3H); 2.38–3.7 (m,6H); 4.65–5.12 (m,3H); 5.34 (s,2H); 6.36 and 6.5 (ss,1H); 7.15–7.75 (m,7H); 8.26 (d,2H) |
| 2-(2-thienyl)ethyl | 5.64 | 1.2 (t,3H); 2.35–3.7 (m,6H); 4.6–5.1 (m,3H); 5.26 (s,2H); 6.25 and 6.38 (ss,1H); 6.7–7.26 (m,3H); 7.44 (d,2H); 8.14 (d,2H) |
| 2-(2-pyridyl)ethyl | 5.63 | 1.2 (t,3H); 2.36–3.56 (m,6H); 4.6–5.1 (m,3H); 5.22 (s,2H); 6.2 and 6.33 (ss,1H); 6.9–7.7 (m,5H); 8.14 (d,2H); 8.46 (m,1H) |
| 2-(1-pyrazolyl)ethyl | 5.62 | 1.24 (m,3H); 2.2–3.7 (m,4H); 4.42–5.22 (m,5H); 5.32 (s,2H); 6.2–6.5 (m,2H); 7.4–7.75 (m,4H); 8.24 (d,2H) |
| 2-(4-methyl-5-thiazolyl)ethyl | 5.64 | 1.24 (t,3H); 2.36–3.64 (m,9H); 4.68–5.18 (m,3H); 5.38 (s,2H); 6.38 and 6.5 (ss,1H); 7.58 (d,2H); 8.28 (d,2H); 8.64 (s,1H) |
| 2-(2-oxo-1-imidazolidinyl)ethyl | 5.66 5.88 | 1.2 (t,3H); 2.36–3.8 (m,10H); 4.5–5.12 (m,3H); 5,32 (s,2H) 6.32 and 6.45 (ss,1H); 7.5 (d,2H); 8.2 (d,2H) |
| 2-(2-oxo-1-pyrrolidinyl)ethyl | 5.66 5.98 | 1.25 (t,3H); 1.7–3.8 (m,12H); 4.58–5.1 (m,3H); 5.26 (s,2H); 6.3 and 6.4 (ss,1H); 7.46 (d,2H); 8.18 (d,2H) |
| 2-(2-thiazolylthio)ethyl | 5.65 | 1.20 (t,3H); 2.36–3.78 (m,6H);.4.72–5.2 (m,3H); 5.33 (s,2H); 6.32 and 6.42 (ss,1H); 7.4–7.72 (m,4H); 8.22 (d,2H) |
| 2-methoxycyclopentyl | 5.62 | 1.0–1.2 (m,3H); 1.4–2.0 (m,6H); 2.2–4.0 (m,5H); 3.3 (s,3H); 5.0 (m,1H); 5.3 (s,2H); 5.7 (m,1H); 6.2 (ss,1H); 7.5 (d,2H); 8.2 (d,2H) |
| 2-methoxycyclohexyl | 5.62 | 1.0–2.0 (m,11H); 2.2–4.0 (m,5H); 3.3 (s,3H); |

TABLE X-continued

| R₁ | IR (microns) | NMR (ppm) |
|---|---|---|
| | | 5.0 (m,1H); 5.4 (m,2H); 5.6 (m,1H); 6.3 (ss,1H); 7.5 (d,2H); 8.2 (d,2H) |
| 2-azidocyclo-hexyl | 4.75 5.65 | 1.0–2.2 (m,11H); 2.2–4.0 (m,5H); 5.0 (m,1H); 5.3 (s,2H); 5.5 (m,1H); 6.4 (ss,1H); 7.5 (d,2H); 8.2 (d,2H) |
| 2-azidocyclo-pentyl | 4.75 5.65 | 1.0–1.5 (m,3H); 1.6–2.2 (m,6H); 2.2–4.0 (m,4H); 4.2 (m,1H); 5.0 (m,1H); 5.3 (s,2H); 5.6 (m,1H); 6.3 (ss,1H); 7.5 (d,2H); 8.2 (d,2H) |
| 3-tetrahydro-furanyl | 5.65 | 1.0–1.6 (m,3H); 2.0–4.0 (m,6H); 4.0 (m,4H); 5.0 (m,1H); 5.4 (s,2H); 6.0 (m,1H); 6.4 (ss,1H); 7.5 (d,2H); 8.2 (d,2H) |
| 1-acetyl-3-pyrrolidinyl | 5.66 | 1.0–1.4 (m,5H); 2.0 (d,3H); 2.2–4.0 (m,8H); 5.0 (m,1H); 5.3 (s,2H); 5.9 (m,1H); 6.4 (ss,2H); 7.5 (d,2H) 8.2 (d,2H) |
| 1-acetyl-3-piperidinyl | 5.66 | 1.0–1.2 (m,3H); 1.4–2.0 (m,4H); 2.0 (s,2H); 2.2–4.0 (m,8H); 5.0 (m,1H); 5.2 (s,2H); 5.4 (m,1H); 6.3 (ss,1H); 7.4 (d,2H); 8.2 (d,2H) |
| 2-tetrahydro-furanylmethyl | 5.66 | 1.0–1.2 (m,3H); 1.6–2.2 (m,4H); 2.2–4.0 (m,4H); 3.8–4.1 (m,3H); 4.6 (m,2H); 5.0 (m,1H); 5.4 (s,2H); 6.4 (ss,1H); 7.6 (d,2H); 8.2 (d,2H) |
| 2-tetrahydro-pyranylmethyl | 5.66 | 1.02–2.04 (m,9H); 2.36–4.08 (m,7H); 4.46 (d,2H); 4.74, 5.0 (m,1H); 5.24 (s,2H); 6.18 and 6.27 (ss,1H); 7.42 (d,2H); 8.14 (d,2H) |
| 1-acetyl-2-pyrrolidinyl-methyl | 5.66 | 1.22 (t,3H); 1.7–2.3 (m,7H); 2.4–3.67 (m,6H); 4.22–5.16 (m,4H); 5.35 (s,2H); 6.32 and 6.42 (ss,1H); 7.5 (d,2H); 8.2 (d,2H) |
| 2-(2-pyridinoyl-amino)ethyl | 5.66 5.98 | 1.25 (t,3H); 2.6 (q,2H); 2.8–4.05 (c,4H); 4.75 (m,2H); 4.95–5.35 (c,4H); 7.2–8.7 (c,9H) |
| 1-formyl-3-piperidyl | 5.65 5.72 | 1.27 (t,3H); 1.46–2.27 (c,4H); 2.4–4.1 (c,8H); 4.7–5.6 (c,4H); 6.3, 6.46 (s,1H); 7.54 (d,2H); 7.88–8.36 (3H) |
| N—methylamino-carbonylmethyl | 5.7 5.98 | 1.2 (m,3H); 2.3–3.68 (c,7H); 4.68–5.38 (c,5H); 6.16, 6.34 (s,1H); 6.78 (b,1H); 7.4 (d,2H); 8.1 (d,2H) |
| 1-aminocarbonyl)ethyl | 5.68 5.9 | 1.06–1.74 (c,6H); 2.36–3.7 (c,4H); 4.76–5.4 (c,3H); 5.6–6.8 (c,4H); 7.54 (d,2H); 8.26 (d,2H) |
| 2-(methoxymethyl-carbonylamino) ethyl | 5.66 5.96 (CH₂Cl₂) | 1.22 (t,3H); 2.62 (q,2H); 3.0–3.95 (c, total 9H) including 3.4 (s,3H) and 3.9 (s,2H); 4.55 (m,2H); 4.8–5.2 (c,1H); 5.32 (s,2H); 6.4 (d,1H); 7.1 (b,1H); 7.55 (d,2H); 8.2 (d,2H) |
| 2-(aminocarbonyloxy) ethyl | 5.66 5.76 | 1.2 (m,3H); 2.6 (q,2H); 2.9–3.6 (c,2H); 4.34 (m,2H); 4.75 (m,2H); 5.05 (b,3H); 5.3 (s,2H); 6.36 (d,1H); 7.5 (d,2H); 8.2 (d,2H) |
| 1,3-dimethoxy-2-propyl | 5.65 | 1.25 (m,3H); 2.6 (m,2H); 2.8–4.3 (c,12H) including 3.35 (s,6H), 4.8 and 5.06 (m,1H); 5.34 (s,2H); 5.9 (m,1H); 6.26 (d,1H); 7.55 (d,2H); 8.26 (d,2H) |
| 2-(2-furylcarbonyl-amino)ethyl | 5.68 6.0 | 1.22 (m,3H); 2.58 (q,2H); 2.8–3.96 (c,4H); 4.65 (m,2H); 4.8–5.2 (c,1H); 5.25 (s,2H); 6.36 (c,2H); 7.06 (d,1H); 7.26 (b,1H); 7.5 (c,3H); 8.2 (d,2H) |
| 1,3-dioxan-5-yl | 5.66 | 1.22 (t,3H); 2.38–3.6 (c,4H); 4.06 (m,4H); 4.66–5.58 (c,6H); 6.16, 6.37 (s,1H); 7.46 (d,2H); 8.2 (d,2H) |
| 1-methyl-2-piperidinon-3-yl | 5.66 6.02 | 1.2 (m,3H); 1.76–2.34 (c,4H); 2.6 (m,2H); 2.95 (s,3H); 3.0–3.6 (c,4H); 5.0 (m,1H); 5.3 (s,2H); 6.06 (m,1H); 6.32 (d,1H); 7.52 (d,2H); 8.2 (d,2H) |
| 1-(aminocarbonyl-methyl)-2-piperidinon-3-yl | 5.68 5.98 | 1.2 (m,3H); 1.7–5.32 (c,16H); 6.0 (b,2H); 6.24 and 6.38 (d,1H); 7.5 (d,2H); 8.2 (d,2H) |
| 2-(2-acetylamino-ethoxy)ethyl | 5.68 6.0 | 1.26 (m,3H); 2.64 (q,2H); 2.86–4.0 (c,8H); 4.72 (m,2H); 4.8 and 5.05 (m,1H); 5.34 (s,2H); 6.38 (d,1H); 6.4 (b,1H); 7.54 (d,2H); 8.24 (d,2H) |
| 2-piperidinon-3-yl | 5.66 5.98 | 1.2 (m,3H); 1.7–3.6 (c,8H); 4.75–5.35 (c,4H); 6.34 (d,1H); 6.74 (b,1H); 7.54 (d,2H); 8.25 (d,2H) |
| 2-pyrrolidinon-3-yl | 5.66 5.85 | 1.24 (m,3H); 2.05–3.62 (c,8H); 4.7–5.2 (c,2H); 5.26 (s,2H); 6.2 and 6.3 (d,1H); 7.44 (c,3H); 8.1 (d,2H) |
| 2-piperidinon-5-yl | 5.65 6.0 | 1.24 (t,3H); 2.0–3.78 (c,11H); 4.8 and 5.0 (m,1H); 5.3 (s,2H); 6.25 and 6.42 (s,1H); 6.96 (b,1H); 7.5 (d,2H); 8.2 (d,2H) |
| 3-methyl-1,3-oxazolid-2-on-4-ylmethyl | 5.66 | 1.22 (t,3H); 2.6 (q,2H); 2.9 (d,3H); 3.0–3.62 (c,2H); 3.9–4.9 (c,5H); 5.02 (m,1H); 5.3 (s,2H); 6.25 and 6.4 (d,1H); 7.5 (d,2H); 8.2 (d,2H) |
| 1,3-dioxolan-4-ylmethyl | 5.67 | 1.24 (m,3H); 2.64 (t,2H); 2.8–4.6 (c,7H); 4.9 (d,2H); 5.1 (m,1H); 5.3 (s,2H); 6.34 (m,1H); 7.5 (d,2H); 8.2 (d,2H) |

PREPARATION C p-Nitrobenzyl 2-(4-ethylthio-3-p-nitrobenzyloxycarbonyloxy-ethyl-2-oxo-1-azetidinyl)-2-1,3-dioxan-5-yl-oxythiocarbonyl-thio)acetate The procedure of Preparation A was employed with p-nitrobenzyl 2-(4-ethylthio-3-p-nitrobenzyloxycarbonyloxyethyl-2-oxo-1-azetidinyl)-2chloroacetate (11.6 g) and potassium 1,3-dioxan-5-yl xanthate (4.8 g) as the starting materials to yield 8.4 g of the title compound. The NMR spectrum in deuterochloroform showed peaks at 1.02–1.56 (c, 6H); 2.6 (m, 2H); 3.4 (m, 1H); 3.6

4.2 (c, 5H); 4.6 5.56 (c, 8H); 6.34 (d, 1H); 7.5 (m, 4H); and 8.2 (m, 4H) ppm.

PREPARATION D

The procedure of Preparation A was employed with compounds of formula V wherein R is p-nitrobenzyloxycarbonyloxyethyl, i is zero, $R_2$ is p-nitrobenzyl, $R_4$ is ethyl and $R_7$ is chloro and the potassium salt of xanthates of the formula $R_1$—O—(C=S)—S— wherein $R_1$ is as shown in Table XI to obtain the corresponding compounds of formula VI whose NMR spectrum is deuterochloroform is shown in Table XI.

TABLE XI

| $R_1$ | NMR (ppm) |
| --- | --- |
| 1-formyl-3-piperidyl (IR(chloroform): 5.64, 5.70, 5.98 microns) | 1.02–2.2 (c,10H); 2.58 (m,2H); 3.1–4.0 (c,5H); 4.67–5.34 (c,6H); 5.52 (m,1H); 6.22, 6.4 (s,1H); 7.44 (m,4H); 7.8–8.2 (c,5H) |
| 1,3-dioxolan-4-ylmethyl | 1.04–1.56 (c,6H); 2.6 3.4 (m,1H); 3.56–4.75 (c,5H); 4.75–5.4 (c,8H); 6.3, 6.4 (s,1H); 7.52 (m,4H); 8.2 (m,4H) |
| 1-methoxy-2-propyl | 1.0–1.6 (c,9H); 2.6 (m,2H); 3.32 (s) and 3.23–3.64 (c,6H); 4.8–5.34 (c,6H); 5.78 (c,1H); 6.3, 6.35 (s,1H); 7.44 (m,4H); 8.18 (m,4H) |
| 1,3-dioxolan-2-ylmethyl | 1.0–1.6 (c,6H); 2.6 (m,2H); 3.36 (m,1H); 3.98 (b,4H); 4.56 (d,2H); 4.96–5.44 (c,7H); 6.34 (s,1H); 7.5 (m,4H); 8.2 (m,4H) |
| 2-pyrrolidinon-3-yl | 1.0–1.6 (c,6H); 2.15–3.0 (c,4H); 3.22–3.62 (c,3H); 4.7–5.42 (c,7H); 6.02 (m,1H); 6.34 (b,1H); 7.5 (m,4H); 8.2 (m,4H) |
| 2-piperidinon-5-yl | 1.0–1.6 (c,6H); 1.9–2.8 (c,6H); 3.36 (m,1H); 3.62 (c,2H); 4.7–5.4 (c,6H); 5.84 (c,1H); 6.26, 6.42 (s,1H); 6.62 (b,1H); 7.5 (m,4H); 8.2 (m,4H) |
| 3-methyl-1,3-oxazolidin-2-on-4-ylmethyl | 1.0–1.6 (c,6H); 2.56 (m,2H); 2.88 (s,3H); 3.12–5.46 (c,12H); 6.0–6.46 (c,1H); 7.46 (m,4H); 8.16 (m,4H) |
| 2-methoxyethyl | 1.06–1.58 (c,6H); 2.6 (m,2H); 3.36 (s) and 3.26–3.8 (c,6H); 4.54–5.4 (c,8H); 6.52 (s,1H); 7.5 (m,4H); 8.2 (m,4) |

PREPARATION E p-Nitrobenzyl 2-(4-ethylthio-3-p-nitrobenzyloxycarbonyloxyethyl-2-oxo-1-azetidinyl)-2-chloroacetate A solution of 11.3 g p-nitrobenzyl 2(4-ethylthio-3-p-nitrobenzyloxycarbonyloxyethyl-2-oxo-1-azetidinyl)-2-hyroxyacetate and 3.02 ml 2,6-lutidine in 175 ml anhydrous tetrahydrofuran was cooled to 0° C. under a nitrogen atmosphere. Thionyl chloride (1.75 ml) was added dropwise and the resulting mixture was stirred at 0° C. for 20 min. The mixture was filtered through Supercel and the filtrate was concentrated in vacuo. The concentrate was dissolved in methylene chloride and the resulting solution was washed successively with 200 ml 1N aqueous hydrochloric acid, 200 ml saturated aqueous sodium bicarbonate solution and 200 ml saturated aqueous sodium chloride solution, dried over anhydrous sodium sulfate and concentrated in vacuo to an oil (11.6 g) of the title compound. The NMR spectrum of the title compound in deuterochloroform showed peaks at 1.04–1.6 (c, 6H); 2.6 (m, 2H); 3.4 (m, 1H); 4.8–5.4 (c, 6H); 5.85, 5.9, 5.98, 6.1 (s, 1H); 7.5 (m, 4H); 8.2 (m, 4H) ppm.

PREPARATION F p-Nitrobenzyl 2-(4-Ethylthio-2-oxo-1-azetidinyl)-2-chloroacetate To a stirred solution of 6.8 g. of p-nitrobenzyl 2-(4-ethylthio-2-oxo-1-azetidinyl)-2-hydroxyacetate in 200 ml. of tetrahydrofuran, at 0°–5° C., was added 2.98 ml. of 2,6-dimethylpyridine, followed by dropwise addition of a solution of 1.73 ml. of thionyl chloride in 20 ml. of tetrahydrofuran, over a 5-minute period. Stirring was continued at 0°–5° C. for 15 minutes, and then the reaction mixture was filtered. The filtrate was evaporated to dryness in vacuo, and the residue was dissolved in 200 ml. of dichloromethane. The resulting solution was washed successively with dilute hydrochloric acid and water, and then dried over anhydrous sodium sulfate. Evaporation in vacuo gave 7.12 g of the title compound as a yellow, viscous liquid. The IR spectrum chloroform of the product showed an absorption at 5.63 microns. The NMR spectrum deuterochloroform of the product showed peaks at 1.3 (t, 3H); 2.47–3.7 (m, 4H); 4.9–5.3 (m, 1H); 5.4 (s, 4H); 6.06 and 6.18 (ss, 1H); 7.58 (d, 2H); and 8.22 (d, 2H) ppm.

PREPARATION G p-Nitrobenzyl 2-(4-Ethylthio-2-oxo-1-azetidinyl)-2-hydroxyacetate A solution of 12.3 g. of 4-ethylthio-2-oxoazetidine and 25.5 g. of p-nitrobenzyl glyoxylate ethyl hemiacetal in 900 ml. of benzene was heated under reflux for 16 hours. During the heating for 16 hours, water and ethanol were removed from the reaction mixture by azeotropic distillation using a Dean-Stark trap. At this point, the benzene was removed by evaporation in vacuo, and the residue was dissolved in 700 ml. of dichloromethane. The dichloromethane solution was washed three times with water, and then dried with anhydrous sodium sulfate. Evaporation in vacuo afforded 32.5 g of the title compound as a yellow semi-solid. The IR spectrum of the product in chloroform showed an absorption at 5.65 microns. The NMR spectrum of the product in deuterochloroform showed peaks at 1.25 (t, 3H); 2.35–3.62 (m, 4H); 4.3 (s, 1H); 4.85 (m, 1H); 5.22 and 5.54 (ss, 1H); 5.38 (s, 2H); 7.5 (d, 2H); and 8.2 (d, 2H) ppm.

PREPARATION H p-Nitrobenzyl 2-(4-ethylthio-3-p-nitrobenzyloxycarbonyloxyethyl-2-oxo-1-azetidinyl)-2-hydroxyacetate 4-Ethylthio-3-p-nitrobenzyloxycarbonyloxyethyl-2-oxo-azetidine (9.0 g), p-nitrobenzyl glyoxylate ethyl hemiacetal (8.15 g) and benzene (350 ml) were heated at reflux for 20 hours under a nitrogen atmosphere using a Dean-Stark water separator. The solution was then concentrated in vacuo and the residue was dissolved in 700 ml of dichloromethane. The dichloromethane solution was washed two times with water, dried over anhydrous sodium sulfate and concentrated in vacuo to a yellowish semi-solid (15.0 g) of the title compound. The NMR spectrum in deuterochloroform showed peaks at 1.02–1.52 (c, 8H); 2.6 (m, 2H); 3.3 (m, 1H); 4.1 (b, 1H); 4.78–5.56 (c, 5H); 7.48 (d, 4H); and 8.18 (d, 4H) ppm. The IR spectrum in dichloromethane showed absorptions at 5.62 and 5.7 microns.

PREPARATION I

4-Ethylthio-2-oxoazetidine

To a solution of 8.0 g. of sodium hydroxide in 200 ml. of water, cooled to 0°–5° C., was added 15.5 ml. of ethanethiol. The cold solution was stirred for 5 minutes, and then a solution of 25.8 g. of 4-acetoxy-2-oxoazetidine in 200 ml. of dichloromethane was added in one portion. The mixture was stirred at 0°–5° C. for 90 minutes, and then the pH was adjusted to 6 using 6N hydrochloric acid. The dichloromethane layer was removed, and the aqueous layer was extracted with further quantities of dichloromethane. The combined dichloromethane solutions were washed with water, followed by saturated sodium chloride, and then they were dried using $Na_2SO_4$. Evaporation in vacuo afforded 23.4 g of the title compound as an oil.

PREPARATION J p-Nitrobenzyl Glyoxylate Ethyl Hemiacetal

A stirred solution of 32.0 g. of the bis(p-nitrobenzyl)ester of tartaric acid in 850 ml. of tetrahydrofuran was cooled to 0°–5° C., and 26.0 g. of periodic acid was added all in one portion. Stirring was continued for 2 hours at 0°–5° C., and then the reaction mixture was filtered. To the filtrate was added 100 ml. of ethanol, and then the resulting solution was evaporated in vacuo. The residue was dissolved in 700 ml. of chloroform, and it was washed successively with concentrated aqueous sodium thiosulfate (5 times) and water (2 times). The chloroform solution was dried using anhydrous sodium sulfate, and then it was evaporated in vacuo to give 25.5 g of the title compound as a viscous liquid.

PREPARATION K

Sodium 2-(Morpholino)ethyl Xanthate

To a stirred solution of 4.91 g. of N-(2-hydroxyethyl)-morpholine in 250 ml. of anhydrous tetrahydrofuran at room temperature was added 1.79 g. of a 50% dispersion of sodium hydride in mineral oil. A precipitate formed. The mixture was stirred for 30 minutes, and then 2.75 ml. of carbon disulfide was added, causing the initial precipitate to dissolve. The reaction mixture was stirred for 30 minutes during which time a further precipitate formed. To the mixture was added 200 ml. of anhydrous ether, and the precipitate was recovered by filtration. The solid was washed with ether, and dried, to give 8.8 g. of the title compound.

PREPARATION L

Potassium 2-(2-oxo-pyrrolidino)ethyl Xanthate

To a stirred solution of 5.16 g. of N-(2-hydroxyethyl)-2-oxo-pyrrolidine in 200 ml. of anhydrous tetrahydrofuran at room temperature was added 4.48 g. of potassium t-butoxide. A gummy precipitate formed. The mixture was stirred for 1 hour, and then 3.6 ml. of carbon disulfide was added. The mixture was stirred for 2 hours, and then 100 ml. of anhydrous ether was added, causing the formation of a gummy precipitate. The solvent was decanted from the gummy precipitate, and the gummy precipitate was dried under high vacuum to give a foam (5.0 g.) of the title compound.

PREPARATION M

4-Ethylthio-3-p-nitrobenzyloxycarbonyloxyethyl-2-oxo-azetidine

To a cooled (0° C.) solution of 572 mg sodium hydroxide in 50 ml. water was added 1.32 ml. of ethanthiol. After 10 minutes a solution of 5.02 g. 4-acetoxy-3-(p-nitrobenzyloxycarbonyloxyethyl)-2-oxo-azetidine in 100 ml. dichloromethane was added and the mixture was stirred vigorously at 0° C. for 30 minutes then at 25° C. for 3 hours. The dichloromethane layer was separated and the aqueous phase was extracted with two 70 ml. portions of dichloromethane. The combined dichloromethane extracts were washed with 70 ml. water, then with 70 ml. saturated aqueous sodium chloride solution, dried over anhydrous sodium sulfate and concentrated in vacuo to an oil. The crude product was purified by column chromatography silica gel, eluting with 5:1 chloroform ethyl acetate, to obtain 4.15 g. of the title compound.

I claim:
1. A compound of the formula

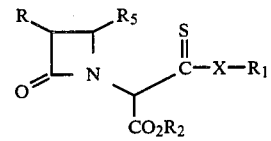

wherein
R is hydrogen, 1-hydroxyalkyl having 1 or 2 carbon atoms or wherein the 1-hydroxyalkyl is substituted with a hydroxyl-protecting group selected from the group consisting of benzyloxycarbonyl, p-nitrobenzyloxycarbonyl, allyloxycarbonyl, 2,2,2-trichloroethoxycarbonyl or trialkylsilyl wherein each alkyl has from 1 to 6 carbon atoms;
$R_1$ is (alk)-G, (alk)-$G_1$,$G_1$ or $CH(G_2)_2$ wherein (alk) is an alkyl group having one to four carbon atoms;
G is hydrogen, alkoxy having one to five carbon atoms, 2-(alkoxy)ethoxy having three to seven carbon atoms, alkylthio having one to five carbon atoms, phenoxy, thiophenoxy, azido, amino, amino substituted with an amino-protecting group selected from the group consisting of benzyloxycarbonyl, p-nitrobenzyloxycarbonyl, allyloxycarbonyl and 2,2,2-trichloroethoxycarbonyl; N-phenyl-N-alkylamino wherein the alkyl has one to four carbon atoms, N-alkanoylamino having two to six carbon atoms, N-alkoxyalkanoylamino having three to ten carbon atoms, 2-(N-alkanoylamino)ethoxy having four to eight carbon atoms, aminocarbonyl, aminocarbonyloxy, N-alkylaminocarbonylamino having two to five carbon atoms, alkanoylaminoacetylamino having four to seven carbon atoms, N-alkylaminocarbonyloxy, aminocarbonylalkoxy having two to five carbon atoms, N-alkylaminocarbonyl having two to five carbon atoms, N-(alkoxyalkyl)aminocarbonyl having three to nine carbon atoms;
$G_1$ is azetidinyl or azetidinyl substituted with N-alkanoyl having two to six carbon atoms or an amine-protecting group selected from the group consisting of benzyloxycarbonyl, p-nitrobenzyloxycarbonyl, allyloxycarbonyl and 2,2,2-trichloroethoxycarbonyl; a five- or six-membered ring which is carbocyclic or heterocyclic having one or two oxygen atoms, one, two three or four nitrogen atoms, a sulfur atom, a nitrogen atom and an oxygen atom or a nitrogen atom and a sulfur atom, or said five- or six-membered ring substituted with alkyl having one to four carbon atoms, dialkyl each having one to four carbon atoms, oxo, amino, amino substituted with an amine-protecting group selected from the group consisting of benzyloxycarbonyl, p-nitrobenzyloxycarbonyl, allyloxycarbonyl and 2,2,2-trichloroethoxycarbonyl; alkoxycarbonyl having two to five carbon atoms, di(alkoxycarbonyl) each having two to five carbon atoms, aminocarbonyl, alkoxyalkyl having two to seven carbon atoms, phenyl, formyl, N-alkylaminocarbonyl having two to five carbon atoms, N-alkylaminocarbonylamino having two to five carbon atoms, alkanoylamino having two to five carbon atoms, alkoxy having one to four carbon atoms or phenoxyacetyl;

$G_2$ is alkanoylaminomethyl each having three to seven carbon atoms or alkoxy each having one to four carbon atoms;

$R_2$ is hydrogen, a group which forms an ester which is hydrolyzed in vivo or a carboxylic acid protecting group selected from the group consisting of benzyl, p-nitrobenzyl, allyl or 2,2,2-trichloroethoxy;

$R_5$ is chloro, bromo or iodo; and

X is oxygen or sulfur.

2. A compound in accordance with claim 1 wherein R is hydrogen, $R_5$ is chloro, X is oxygen and $R_1$ is methyl, ethyl, 2-methoxyethyl, 2-ethoxyethyl, 1-methoxy-2-propyl, bis(methoxymethyl)methyl, 2-(2-methoxyethoxy)ethyl, 2-azidoethyl, aminocarbonylmethyl, 1-(aminocarbonyl)-1-ethyl, 1-(N-methylaminocarbonyl)-1-ethyl, bis(acetylaminomethyl)methyl, 2-(aminocarbonylmethoxy)ethyl, 2-(N-methylaminocarbonyloxy)ethyl, 1-(N-(2-methoxyethyl)aminocarbonyl)-1-ethyl, 2-(aminocarbonyloxy)ethyl, 2-(N-methylaminocarbonylamino)ethyl, 2-(methoxymethylcarbonylamino)ethyl, 2-(acetylaminoacetylamino)ethyl, 2-(2-acetylaminoethoxy)ethyl, 1-acetylamino-2-propyl, 2-(acetylamino)ethyl, 2-azidocyclohexyl, 2-methoxycyclohexyl, 2-formylaminocyclohexyl, 2-acetylaminocyclohexyl, 2-(N-methylaminocarbonylamino)-cyclohexyl, 2-methoxycyclopentyl, 1-acetyl-3-azetidinyl, 1-acetyl-3-pyrrolidinyl, 1-ethylcarbonyl-3-pyrrolidinyl, 1-formyl-3-pyrrolidinyl, 2-pyrrolidon-3-yl, 3-tetrahydrofuranyl, 2-tetrahydrofuranylmethyl, 2-(1-imidazolyl)ethyl, 2-(4-methoxycarbonyl-1,2,3-triazolyl)ethyl, 2-(4,5-dimethoxycarbonyl-1,2,3-triazolyl)ethyl, 2-(4-aminocarbonyl-1H-1,2,3-triazolyl)ethyl, 1,3-dioxolan-2-ylmethyl, 1,3-dioxolan-4-ylmethyl, 2,2-dimethyl-1,3-dioxolan-4-ylmethyl, 3-methyl-1,3-oxazolid-2-on-4-ylmethyl, 2-(2H-1,2,3,4-tetrazol-2-yl)ethyl, 2-piperidon-5-yl, 1-methyl-2-piperidon-3-yl, 1-formyl-3-piperidyl, 1-formyl-4-piperidyl, 1-acetyl-3-piperidyl, 1-phenoxymethylcarbonyl-3-piperidyl, 1-ethylcarbonyl-3-piperidyl, 1-aminocarbonyl-3-piperidyl, 1-aminocarbonylmethyl-2-piperidon-3-yl, 2-perhydropyrimidinon-5-yl, 1,3-dioxan-5-yl, 2-phenyl-1,3-dioxan-5-yl, 2-methoxymethyl-1,3-dioxan-5-yl, 2-phenoxyethyl, 2-thiophenoxyethyl, 2-phenethyl, 2-(2-thienyl)ethyl, 2-(2-pyridyl)ethyl, 3-(3-pyridyl)propyl, 2-(pyrazol-1-yl)ethyl, 2-(4-methylthiazol-5-yl)ethyl, 2-(2-thiazolylthioethyl)ethyl, 2-(N-methylanilino)ethyl, 2-(2-tetrahydropyranyloxy)ethyl, 2-tetrahydropyranylmethyl, 2-(1-morpholino)ethyl, 2-azido-2-phenethyl, 1-acetyl-2-pyrrolidylmethyl, 2-(2-pyrrolidon-1-yl)ethyl, 2-(2-pyridinoylamino)ethyl, 2-(2-furanoylamino)ethyl, 2-(2-imidazolidinon-1-yl)ethyl, 2-piperidon-3-yl or 2-(2-piperidon-1-ylacetylamino)ethyl.

3. A compound in accordance with claim 2 wherein $R_2$ is p-nitrobenzyl.

4. A compound in accordance with claim 1 wherein R is 1-hydroxyethyl or 1-hydroxyethyl substituted with a hydroxyl-protecting group, X is oxygen and $R_1$ is 1-formyl-3-piperidinyl, 1,3-dioxan-5-yl, 1,3-dioxan-2-yl methyl, 1,3-dioxolan-2-ylmethyl, 1,3-dioxolan-4-ylmethyl, 2-piperidinon-3-yl, 2-piperidinon-5-yl, 2-pyrrolidinon-3-yl, 1-methoxy-2-propyl, 2-methoxyethyl, 3-methyl-1,3-oxazolidin-2-on-4-ylmethyl, 2-tetrahydropyranylmethyl, 1-methyl-2-piperidinylmethyl or 2-(4-acetyl-1-piperazinyl)ethyl.

5. A compound in accordance with claim 4 wherein $R_2$ is p-nitrobenzyl.

6. A compound in accordance with claim 1 wherein R is hydrogen, $R_5$ is chloro, X is oxygen and $R_1$ is 2-azidoethyl, 2-aminoethyl, 1-azido-2-propyl, 1-amino-2-propyl, 1-p-nitrobenzyloxycarbonyl-3-pyrrolidinyl, 3-pyrrolidinyl, 1-p-nitrobenzyloxycarbonyl-3-piperidinyl, 3-piperidinyl, 1-p-nitrobenzyloxycarbonyl-2-pyrrolidinylmethyl, 2-pyrrolidinylmethyl or 2-aminocyclohexyl.

7. A compound in accordance with claim 6 wherein $R_2$ is p-nitrobenzyl.

8. A compound in accordance with claim 1 wherein the group which form an ester $R_2$ hydrolyzable in vivo is alkanoyloxymethyl having from 3 to 8 carbon atoms, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-[alkoxycarbonyl]amino)ethyl having from 4 to 10 carbon atoms, 3-phthalidyl, 4-crotonolactonyl, gamma-butyrolacton-4-yl or carboxyalkylcarbonyloxymethyl having from 4 to 12 carbon atoms.

* * * * *